US007579005B2

(12) United States Patent
Keeler et al.

(10) Patent No.: US 7,579,005 B2
(45) Date of Patent: Aug. 25, 2009

(54) PROCESS FOR RECOMBINANT EXPRESSION AND PURIFICATION OF ANTIMICROBIAL PEPTIDES USING PERIPLASMIC TARGETING SIGNALS AS PRECIPITABLE HYDROPHOBIC TAGS

(75) Inventors: Sharon Jo Keeler, Bear, DE (US); Sheryl M. Wolstenholme, Elkton, MD (US); Jodie L. Duke, Newark, DE (US); Linda L. Hnatow, Oxford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/287,809

(22) Filed: Nov. 28, 2005

(65) Prior Publication Data

US 2007/0122425 A1 May 31, 2007

(51) Int. Cl.
*A61K 39/00* (2006.01)
*A61K 39/38* (2006.01)
*A61K 39/085* (2006.01)

(52) U.S. Cl. ...................... 424/192.1; 424/9.1; 424/9.2; 424/93.2; 424/184.1; 424/200.1; 424/234.1; 424/278.1; 424/282.1; 435/41; 435/69.8

(58) Field of Classification Search .................. 424/9.1, 424/9.2, 184.1, 192.1, 193.1, 200.1, 234.1, 424/278.1, 282.1, 93.2; 435/41, 69.1
See application file for complete search history.

(56) References Cited

U.S. PATENT DOCUMENTS 4,683,202 A 7/1987 Mullis
4,874,702 A 10/1989 Fiers et al.
5,589,364 A 12/1996 Williams et al.
5,851,802 A 12/1998 Better

FOREIGN PATENT DOCUMENTS

CA 1 207 251 7/1986
EP 0 041 767 B1 12/1981
WO WO 89/10971 A1 11/1989

OTHER PUBLICATIONS

K. Terpe, Overview of Tag Protein Fusions: From Molecular and Biochemical Fundamentals to Commercial Systems, Appl. Microbiol. Biotechnol., vol. 60:523-533, 2003.

Tomas Moks et al., Large-Scale Affinity Purification of Human Insulin-Like Growth Factor I From Culture Medium of *Escherichia coli*, Bio/Technology, vol. 5:379-382, 1987.

Hermann Gram et al., A Novel Approach for High Level Production of a Recombinant Human Parathyroid Hormone Fragment in *Escherichia coli*, Bio/Technology, vol. 12:1017-1023, 1994.

Martin Mieschendahl et al., A Novel Prophage Independent TRP Regulated Lambda PL Expression System, Bio/Technology, vol. 4:802-806, 1986.

Swee Lay Thein et al., The Use of Synthetic Oligonucleotides as Specific Hybridization Probes in the Diagnosis of Genetic Disorders, Chapter 3, pp. 33-50, 1986.

Susan Gottesman, Minimizing Proteolysis in *Escherichia coli*: Genetic Solutions, Methods in Enzymology, vol. 185:119-129, 1990.

R. B. Merrifield, Solid Phase Peptide Synthesis. I. The Synthesis of a Tetrapeptide, J. Am. Chem. Soc., vol. 85:2149-2154, 1963.

Jui-Yoa Chang, Thrombin Specificity—Requirement for Apolar Amino Acids Adjacent to the Thrombin Cleavage Site of Polypeptide Substrate, Eur. J. Biochem., vol. 151:217-224, 1985.

Stephen F. Altschul et al., Basic Local Alignment Search Tool, J. Mol. Biol., vol. 215:403-410, 1990.

Shaorong Chong et al., Single-Column Purification of Free Recombinant Proteins Using a Self-Cleavable Affinity Tag Derived From a Protein Splicing Element, Gene, vol. 192:271-281, 1997.

Kevin L. Piers et al., Recombinant DNA Procedures for Producing Small Antimicrobial Cationic Peptides in Bacteria, Gene, vol. 134:7-13, 1993.

Nicolas Groch et al., Synthesis of the *Bacillus subtilis* Histone-Like DNA-Binding Protein HBSU NI *Escherichia coli* and Secretion Into the Periplasm, Gene, vol. 124:99-103, 1993.

Tomas Kempe et al., Multiple-Copy Genes: Production and Modification of Monomeric Peptides From Large Multimeric Fusion Proteins, Gene, vol. 39:239-245, 1985.

Neus Cols et al., Secretion of Mouse-Metallothionein by Engineered *E. coli* Cells in Metal-Enriched Culture Media, J. Mol. Microbiol., vol. 3(4):507-512, 2001.

William R. Pearson, Searching Protein Sequence Databases—Is Optimal Best?, Computational Methods in Genome Research, Proc. Int. Symp., 1994 pp. 111-120, Editor: Suhai, Sandor., Publisher: Plenum, Ney Work, NY.

Alfred L. Goldberg et al., The Selective Degradation of Abnormal Proteins in Bacteria, Maximizing Gene Expression, Chapter 9, pp. 287-314, 1986.

Mukund V. Deshpande, Ethanol Production From Cellulose by Coupled Saccharification/Fermentation Using *Saccharomyces cerevisiae* and Cellulase Complex from *Sclerotium rolfsii* UV-8 Mutant, Applied Biochemistry and Biotechnology, vol. 36:227-234, 1992.

Helen B. Forrester et al., Amplification of DNA Sequences up to 5 KB From Small Amounts of Genomic DNA Using Tub DNA Polymerase, Methods in Molecular Biology, vol. 15:31-39, B. A. White, Edition, 1993.

*Primary Examiner*—Rodney P. Swartz
(74) *Attorney, Agent, or Firm*—Christine M. Lhulier

(57) ABSTRACT

A process was developed for expressing antimicrobial peptides in a recombinant host cell that eliminates host cell toxicity and antimicrobial peptide degradation, as well as providing a process for rapid purification. Fusion proteins comprising a periplasmic targeting signal, cleavage site, and antimicrobial peptides provide the basis for this process which produces antimicrobial peptides that may be used in antimicrobial compositions and articles.

10 Claims, 6 Drawing Sheets

A

B

Figure 1:
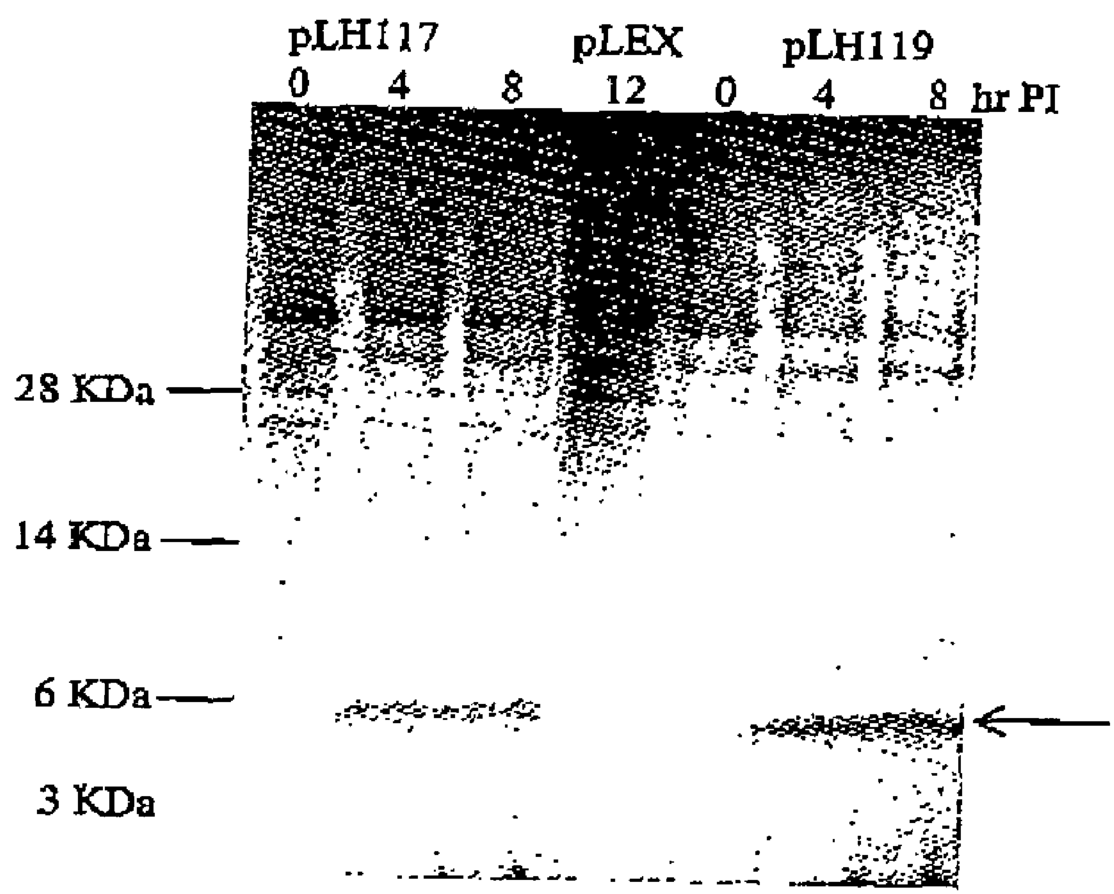

PROCESS FOR RECOMBINANT EXPRESSION AND PURIFICATION OF ANTIMICROBIAL PEPTIDES USING PERIPLASMIC TARGETING SIGNALS AS PRECIPITABLE HYDROPHOBIC TAGS

FIELD OF THE INVENTION

This invention relates to the field of antimicrobial peptides. More specifically, the invention relates to the recombinant production of antimicrobial peptides using a bacterial periplasmic targeting signal as a fusion partner in a recombinant production system.

BACKGROUND OF THE INVENTION

Antimicrobial properties are desired in a wide range of materials including those in medical devices, personal care items, surfaces related to food handling, and locations such as hospitals and nursing homes where people have lowered resistance to infection. For use in such applications, antimicrobial peptides must be produced on a large scale.

Although short (<20 amino acid) peptides can be produced in high yields via chemical synthesis (Merrifield, R. B., J. Am. Chem. Soc., 85:2149-2154 (1993)), recombinant production offers the potential for large scale production at a more reasonable cost. However, the expression of short polypeptide chains can be problematic in microbial systems because small peptides are often proteolyzed by the host cell's protein regeneration systems. The expression of antimicrobial peptides is often even more problematic because the peptides can be toxic to the production host cells, leading to limited production and cell death (S. Gottesman, Methods in Enzymology 185:119-129 (1990); Goff and Goldberg, in *Maximizing Gene Expression* p 287-314, (1986)). Fusion of peptides to larger carrier proteins, which serve as anionic partners can eliminate toxicity, provide stability, and provide a method of affinity purification (K. Terpe, Appl. Microbiol. Biotechnol. Vol. 60: 523-533 (2003)). However, even when the toxic peptide is part of a larger fusion protein, high concentrations of fusion peptide in a cell can lead to toxic effects.

Toxicity and proteolytic degradation have been avoided by using a fusion partner, which promotes aggregation of the fusion protein into insoluble inclusion bodies. Inclusion bodies protect against proteolysis and serve as a purification substrate (T. Kempe et al., Gene v39:239-245 (1985)). Alternatively, carrier proteins designed to direct secretion of the fusion proteins into the medium, allowing recovery of the target fusion proteins directly from the medium, have also been used to overcome production issues. For example, U.S. Pat. No. 5,851,802 describes a series of recombinant peptide expression vectors for peptide fusion secretion. A disadvantage of fusion systems is that they generally require costly cleavage reagents and affinity columns for purification.

Periplasmic targeting sequences have been used to direct heterologous proteins into the periplasmic space of *E. coli* (Groch, et al., Gene v124: 99-103 (1993)) or into the medium using the cell's secretion system (Cols et al., J. of Molec. Microbiol. and Biotech. v3:507-512 (2001); WO 8910971).

There remains a need for a production expression system for antimicrobial peptides, which avoids toxicity and proteolytic degradation, as well as allows for simple, inexpensive recovery of the peptide.

SUMMARY OF THE INVENTION

The present invention provides a process for producing an antimicrobial peptide (AMP) that includes expressing the AMP as a fusion protein with a periplasmic targeting signal. The process comprises the steps of:

a) providing a transformed host cell comprising an isolated nucleic acid fragment under the control of suitable regulatory sequences, the isolated nucleic acid fragment encoding a fusion protein, the fusion protein comprising a periplasmic targeting signal and at least one antimicrobial peptide;
b) growing the host cell of (a) under suitable conditions whereby the fusion protein is expressed;

Additional Process Steps May Include:

a) purifying the fusion protein;
b) cleaving the fusion protein to produce products comprising the antimicrobial peptide and periplasmic targeting signal; and
c) isolating the antimicrobial peptide from the periplasmic targeting signal.

In addition, the invention provides a composition comprising a fusion protein comprising a periplasmic targeting signal and at least one antimicrobial peptide.

In other embodiments the invention provides an isolated nucleic acid fragment encoding the composition of the invention, a chimeric gene comprising the isolated nucleic acid, a vector and a transformed host cell each comprising the chimeric gene, and antimicrobial compositions and antimicrobial articles comprising the antimicrobial peptide derived from the composition of the invention.

BRIEF DESCRIPTION OF THE DRAWINGS AND SEQUENCE DESCRIPTIONS

The invention can be more fully understood from the following detailed description, the figures, and the accompanying sequence descriptions that form a part of this application.

FIG. 1. Stained blot of PAGE of protein samples from shake flask study using strains containing pLH117 (GeneIII targeting signal-16KGLG1-6His) or pLH119 (OmpA targeting signal-16KGLG1-6His).

Figure 2:
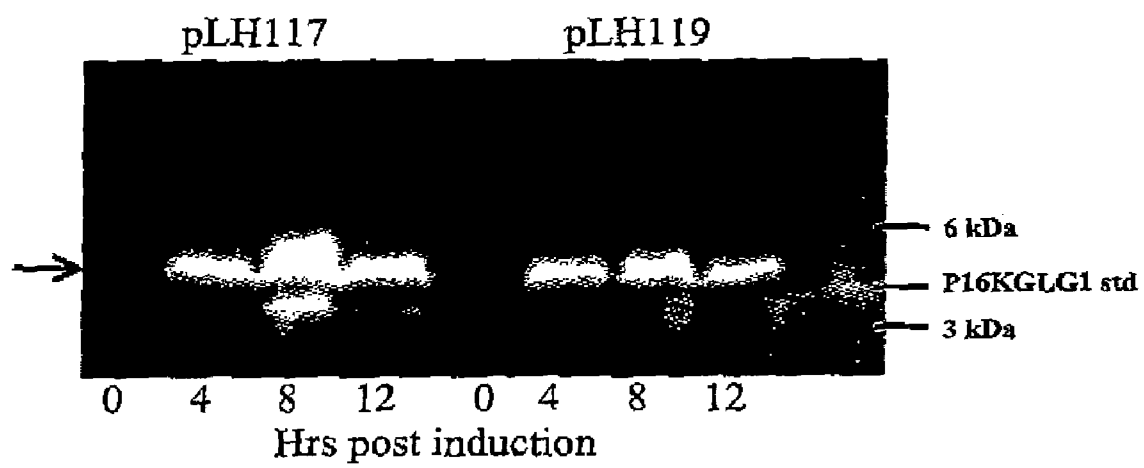

FIG. 2. Western blot of PAGE of protein samples from fermentation of strains containing pLH117 (GeneIII targeting signal-16KGLG1-6His) or pLH119 (OmpA targeting signal-16KGLG1-6His) using anti-6His antibody. (Arrow designates recombinant fusion peptide.)

Figure 3:
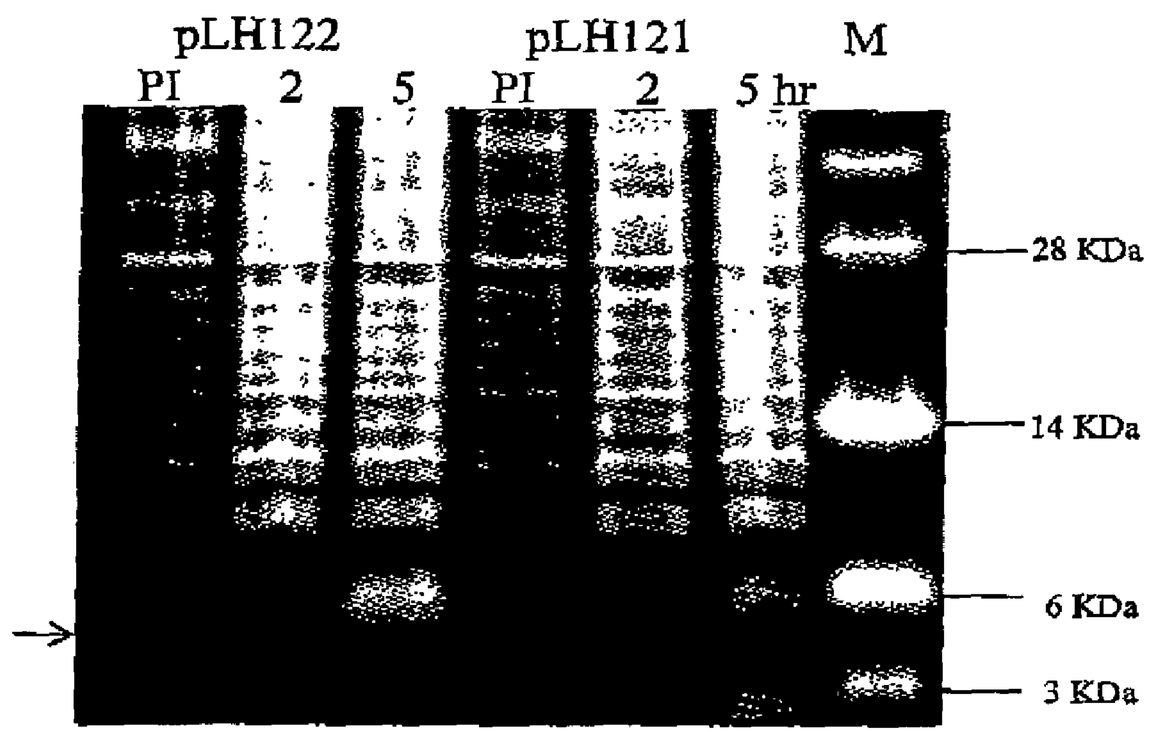

FIG. 3. Stained PAGE of proteins samples from shake flask study using strains containing pLH122 (GeneIII targeting signal-Cleavage site-16KGLG1) or pLH121 (OmpA targeting signal-Cleavage site-16KGLG1). (Arrow designates recombinant fusion peptide.)

Figure 4:
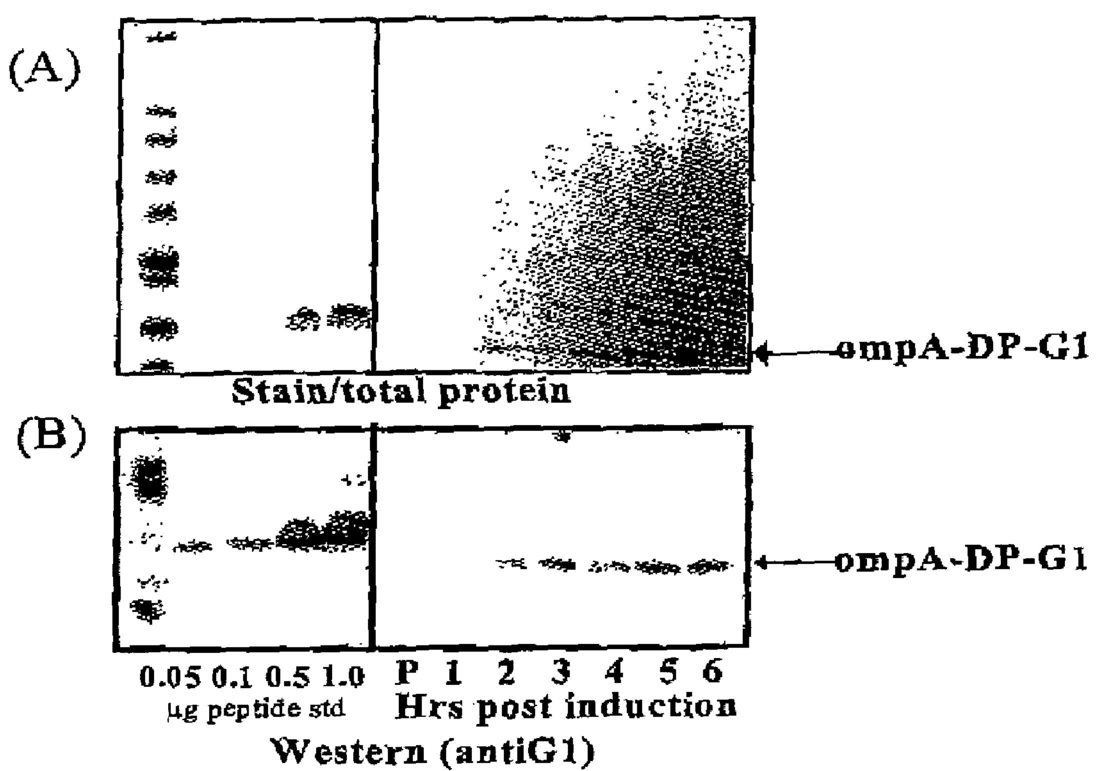

FIG. 4. PAGE of protein samples from fermentation of LH121 (OmpA targeting signal-Cleavage site-16KGLG1) showing: A) MemCode stain, and B) Western.

Figure 5:
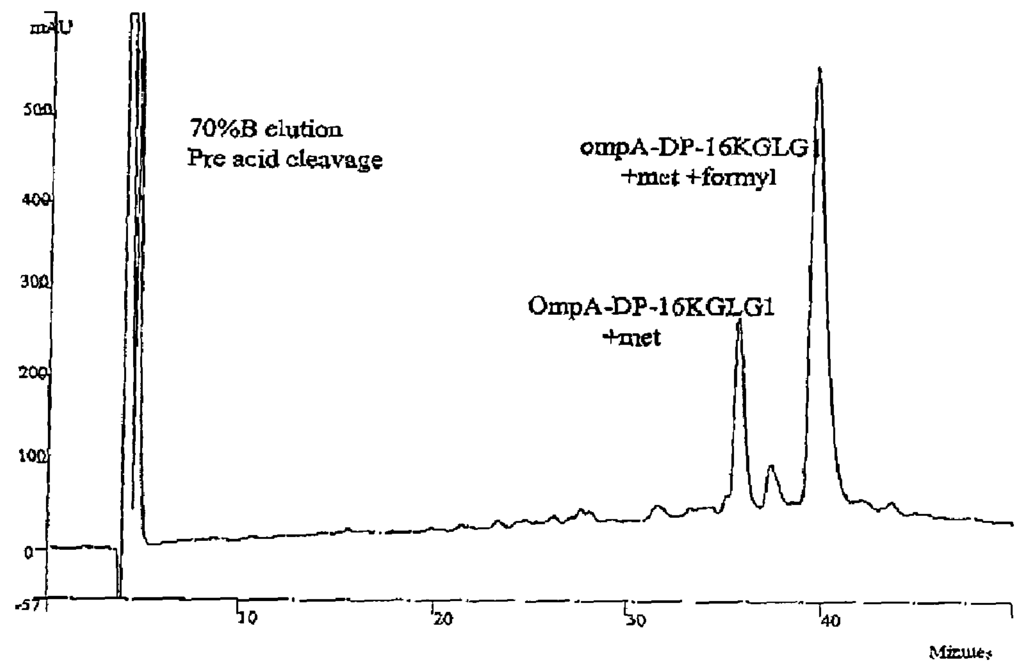
Figure 5:
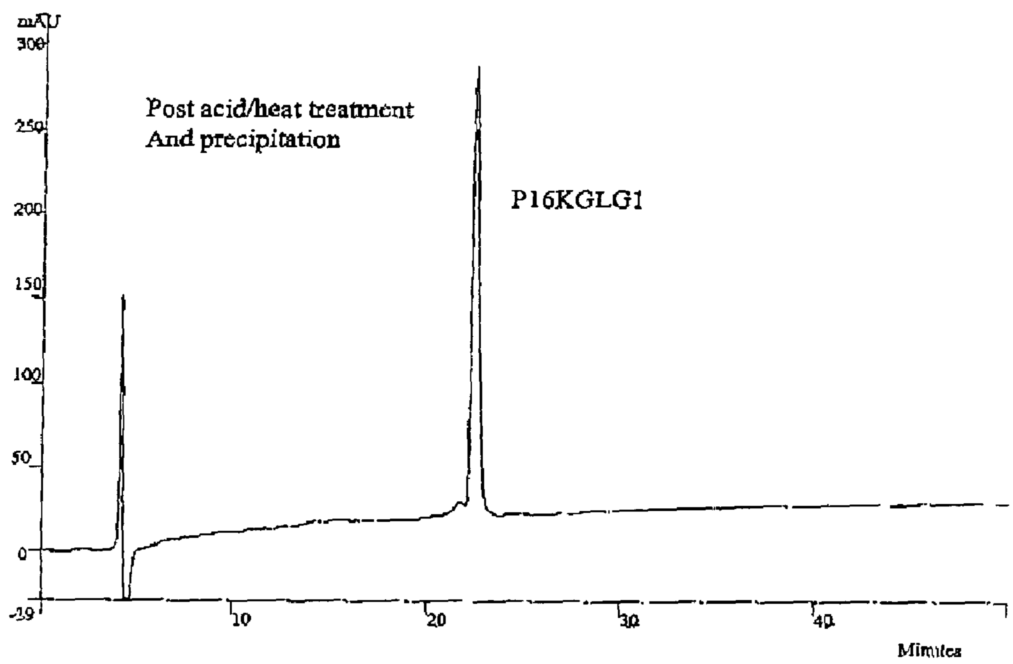

FIG. 5. RP-HPLC analytical chromatography of: A) sample from the 70% B extraction post evaporation, and B) purified 16KGLG1 peptide following acid treatment.

Figure 6:
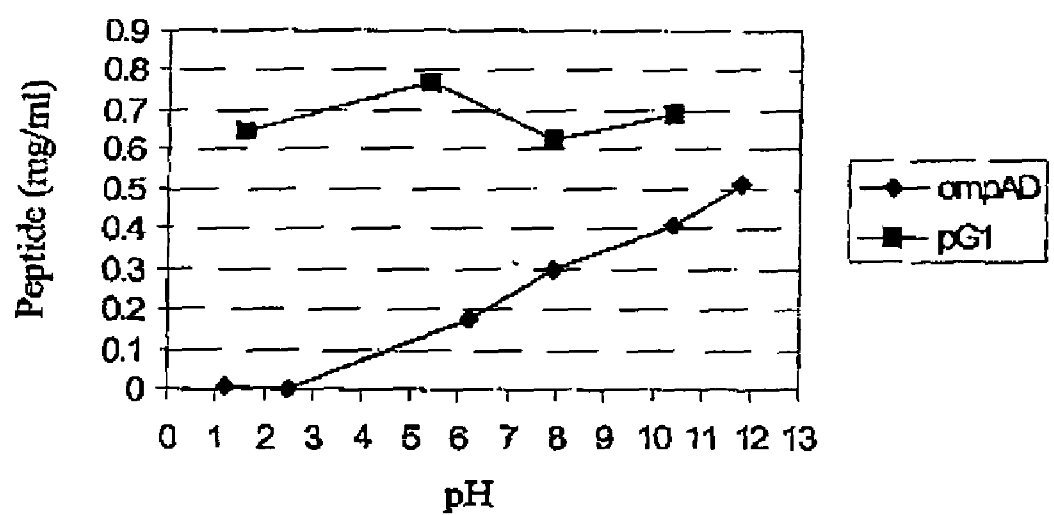

FIG. 6. Comparison of OmpAD targeting signal peptide and P16KGLG1 peptide solubility over a range of pH. (Mg/ml refers to peptide in solution.)

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. § 1.822.

SEQ ID NO:1 is the amino acid sequence of the 16KGLG1 Antimicrobial peptide.

SEQ ID NO:2 is the amino acid sequence of the OmpA periplasmic targeting signal peptide.

SEQ ID NO:3 is the amino acid sequence of the GeneIII periplasmic targeting signal peptide.

SEQ ID NO:4 is the amino acid sequence of the OmpA targeting signal-DP-16KGLG1 fusion protein.

SEQ ID NO:5 is the amino acid sequence of the GeneIII targeting signal-DP-16KGLG1 fusion protein.

SEQ ID NO:6 is the amino acid sequence of the OmpA targeting signal-16KGLG1-6His fusion protein.

SEQ ID NO:7 is the amino acid sequence of the GeneIII targeting signal-16KGLG1-6His fusion protein.

SEQ ID NO:8 is a nucleotide sequence encoding the 16KGLG1 peptide.

SEQ ID NO:9 is a nucleotide sequence encoding the OmpA periplasmic targeting signal peptide.

SEQ ID NO:10 is a nucleotide sequence encoding the GeneIII periplasmic targeting signal peptide.

SEQ ID NO:11 is a nucleotide sequence encoding the OmpA targeting signal sequence-16KGLG1-6His fusion protein.

SEQ ID NO:12 is a nucleotide sequence encoding the GeneIII targeting signal sequence-16KGLG1-6His fusion protein.

SEQ ID NO:13 is a nucleotide sequence encoding the OmpA targeting signal sequence-DP-16KGLG1 fusion protein.

SEQ ID NO:14 is a nucleotide sequence encoding the GeneIII targeting signal sequence-DP-16KGLG1 fusion protein.

SEQ ID NO:15 is the amino acid sequence of the OmpA periplasmic targeting signal cleavage peptide.

SEQ ID NO:16 is the amino acid sequence of the 16KGLG1 cleavage peptide.

SEQ ID NOs:17-22 are primers annealed to prepare a DNA fragment encoding the OmpA targeting signal-16KGLG1-6His fusion protein.

SEQ ID NOs:23-24 are PCR primers used to amplify the DNA fragment prepared by annealing SEQ ID NOs:17-22.

SEQ ID NO:25 is the nucleotide sequence of the prepared DNA fragment encoding the OmpA targeting signal sequence-16KGLG1-6His fusion protein.

SEQ ID NOs:26-27 are primers used to sequence the insert in pLH119.

SEQ ID NOs:28-33 are PCR primers used in preparing a DNA fragment encoding the GeneIII targeting signal-16KGLG1-6His fusion protein.

SEQ ID NO:34 is the nucleotide sequence of the prepared DNA fragment encoding the GeneIII targeting signal sequence-16KGLG1-6His fusion protein.

SEQ ID NOs:35-40 are PCR primers used in preparing a DNA fragment encoding the OmpA targeting signal-DP-16KGLG1 fusion protein.

SEQ ID NO:41 is the nucleotide sequence of the prepared DNA fragment encoding the OmpA targeting signal sequence-DP-16KGLG1 fusion protein.

SEQ ID NOs:42-47 are PCR primers used in preparing a DNA fragment encoding the GeneIII targeting signal-DP-16KGLG1 fusion protein.

SEQ ID NO:48 is the nucleotide sequence of the prepared DNA fragment encoding the GeneIII targeting signal sequence-DP-16KGLG1 fusion protein.

DETAILED DESCRIPTION OF THE INVENTION

The present invention describes a process for recombinantly producing and then isolating antimicrobial peptides (AMPs). Such peptides include linear, cationic, amphiphilic, alpha helical AMPs. The AMPs are expressed as fusion proteins including a periplasmic targeting signal and one or more antimicrobial peptides. Chimeric genes encoding such fusion proteins and containing suitable regulatory sequences, DNA constructs containing these chimeric genes, as well as the fusion proteins themselves are the subjects of this invention. Additionally, the invention provides recombinant organisms transformed with the chimeric genes of the instant invention; the chimeric genes may be integrated into the chromosome or plasmid-borne.

It was found that a fusion protein of the present invention consisting of a periplasmic targeting signal and an AMP was not targeted to the periplasmic space, but was retained within the bacterial cell. Addition of the periplasmic targeting signal to the AMP stabilized and detoxified the AMP within the bacterial cell. The fusion proteins of the invention were not toxic to the expression host and were not subject to proteolysis by the expression host. It was also found that following cleavage to separate the AMP and the targeting signal peptide, the AMP was effectively isolated from the periplasmic targeting signal by differential precipitation.

In this disclosure, a number of terms and abbreviations are used. The following definitions and explanations are provided.

"Polymerase chain reaction" is abbreviated PCR.

"High performance liquid chromatography" is abbreviated HPLC.

"Reverse-phase high performance liquid chromatography" is abbreviated RP-HPLC.

"Sodium dodecyl sulfate" is abbreviated SDS.

"Sodium dodecyl sulfate-polyacrylamide gel electrophoresis" is abbreviated SDS-PAGE.

"Ethylene diamine tetraacetic acid" is abbreviated EDTA.

"Bovine serum albumin" is abbreviated BSA.

"Deoxyribonucleotide triphosphates" is abbreviated dNTPs.

"Time-of-flight" is abbreviated TOF.

"Antimicrobial peptide" is abbreviated AMP.

As used herein the following abbreviations will be used to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamine acid | Glu | E |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |

-continued

| Amino Acid | Three-Letter Abbreviation | One-Letter Abbreviation |
|---|---|---|
| Threonine | Thr | T |
| Tryptophan | Trp | W |
| Tyrosine | Tyr | Y |
| Valine | Val | V |

The terms "amphiphilic" and "amphipathic" peptides are used interchangeably herein and refer to peptides which have regions or sequences of hydrophilic and hydrophobic amino acid residues.

The term "concatemer" herein refers to multiple copies of a given unit as tandem repeats. The multiple copies (multimers) may be separated by intervening sequences that provide, for example, cleavage sites for post-expression peptide recovery.

The terms "protein", "oligopeptide" and "polypeptide" are used interchangeably herein. A "fusion protein", "fusion oligopeptide" or "fusion polypeptide" refers to a protein that has two or more joined parts, such as a signal sequence peptide and at least one antimicrobial peptide.

The term "back-translate" refers to deducing the nucleotide sequence encoding a given amino acid sequence, optionally taking into account organism-specific codon preferences, from a given amino acid sequence.

The term "isolated nucleic acid fragment" or "isolated nucleic acid molecule" refers to a polymer of RNA or DNA that is single-or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "periplasmic targeting signal-AMP fusion protein" is a protein having a periplasmic targeting signal and an antimicrobial peptide. In addition, this fusion protein has a cleavage site between the periplasmic targeting signal and the antimicrobial peptide. Also, the fusion protein may have multiple AMPs, either identical to each other, or of differing identities. Cleavage sites located between multiple AMPs are optional, but preferred.

"Codon degeneracy" refers to divergence in the genetic code permitting variation of the nucleotide sequence without affecting the amino acid sequence of an encoded polypeptide. Accordingly, the instant invention relates to any nucleic acid fragment that encodes all or a substantial functional portion of the amino acid sequence of a periplasmic targeting signal-AMP fusion protein.

The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell. Accordingly, in the instant invention, codon bias for enteric bacteria may be used as a basis for synthesizing the nucleic acid sequences encoding periplasmic targeting signal-AMP fusion proteins, such that optimal expression would be obtained in *E. coli*.

"Synthetic genes" or "fusion genes" can be assembled from oligonucleotide building blocks that are chemically synthesized using procedures known to those skilled in the art. These building blocks are ligated and annealed to form gene segments that are then enzymatically assembled to construct the entire gene. The instant invention describes fusion genes that are created comprising a nucleotide sequence encoding a periplasmic targeting signal and a nucleotide sequence encoding at least one AMP. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites, and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. Moreover, alterations in a nucleic acid fragment, which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Each of the proposed modifications is well within the routine skill in the art, as is determination of retention of biological activity of the encoded products, and may be present in "substantially similar" nucleic acids.

The term "signal peptide" or "targeting signal" refers to an amino terminal polypeptide preceding a secreted mature protein. The signal peptide is cleaved from and is therefore not present in the mature protein. Signal peptides have the function of directing and translocating secreted proteins across cell membranes.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes, which are not part of the central metabolism of the cell, and usually in the form of circular double-stranded DNA molecules. Such elements may be autonomously replicating sequences, or genome integrating sequences, derived from any source, in which a number of nucleotide sequences have been joined or recombined into a unique construction which is capable of introducing a promoter fragment and DNA sequence for a selected gene product along with appropriate 3' untranslated sequence into a cell The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990)), DNASTAR (DNASTAR, Inc., Madison, Wis.), and the FASTA program incorporating the Smith-Waterman algorithm (W. R. Pearson, *Comput. Methods Genome Res*., [Proc. Int. Symp.] (1994), Meeting Date 1992, 111-20. Editor(s): Suhai, Sandor. Publisher: Plenum, New York, N.Y.). Within the context of this application it will be understood that where sequence analysis software is used for analysis, the results of the analysis will be based on the "default values" of the program referenced, unless otherwise specified. As used herein "default values" will mean any set of values or parameters that originally load with the software when first initialized. More preferred amino acid fragments are those that are at least about 90% identical to the sequences herein using a BLASTP analysis, where about 95% is preferred. Similarly, preferred nucleic acid sequences corresponding to the sequences herein are those encoding active proteins and which are at least 90% identical to the nucleic acid sequences reported herein. More preferred nucleic acid fragments are at least 95% identical to the sequences herein.

Antimicrobial Peptides

The antimicrobial peptides (AMPs) that are useful for the fusion proteins of the instant invention comprise linear, cationic, amphiphilic, alpha helical AMPs. Preferred are cathelicidins, magainins, cecropins and other natural peptides having similar properties. In addition, synthetic peptides which have properties similar to those of cathelicidins, magainins, and/or cecropins are preferred in the invention. For example, non-natural antimicrobial peptide compositions are described in WO 2005/019241, including the 16KGLG1 peptide (SEQ ID NO:1). It is preferred that the linear, cationic, amphiphilic, α-helical AMP comprises less than 50 amino acids and has a molecular weight of less than 6,000 daltons. It is more preferred that the linear, cationic, amphiphilic, α-helical AMP comprises less than 30 amino acids.

Periplasmic Targeting Signals

Periplasmic targeting signal peptide sequences (also called targeting signals or signal sequences) usually are present on the N-terminus of bacterial secretory proteins. They vary in length from about 15 to about 70 amino acids. The primary sequences of amino acids also vary, but generally have a common overall structure including the following parts: i) the N-terminal part has a variable length and generally carries a net positive charge; ii) following is a central hydrophobic core of about 6 to about 15 amino acids; and iii) the final part includes four to six amino acids which define the cleavage site for signal peptidases.

Periplasmic targeting signal peptide sequences suitable for use in the present invention are generally derived from a protein that is secreted in a Gram negative bacterium. The secreted protein may be encoded by the bacterium, or by a bacteriophage, which infects the bacterium. Examples of suitable Gram negative bacterial sources of secreted proteins include but are not limited to, members of the genera *Escherichia, Pseudomonas, Klebsiella, Salmonella, Caulobacter, Methylomonas, Acetobacter, Achromobacter, Acinetobacter, Aeromonas, Agrobacterium, Alcaligenes, Azotobacter, Burkholderia, Citrobacter, Comamonas, Enterobacter, Erwinia, Rhizobium, Vibrio* and *Xanthomonas*. For example, bacteriophages M13 and fd infect Gram negative bacteria and encode proteins secreted by the Gram negative bacterium.

Examples of bacterial secreted proteins having periplasmic targeting signal peptides include, but are not limited to, proteins encoded by the following genes: ompA, geneIII, *E. coli* alkaline phosphatase, lamb, male, secE, secY, and prlA-4. Preferred are the periplasmic targeting signal peptides from OmpA of *E. coli* (SEQ ID NO:2) and GeneIII of bacteriophage fd (SEQ ID NO:3). One skilled in the art can easily identify the periplasmic targeting signal peptide located at the N-terminus of each of these proteins, and of other bacterial secretory proteins. It is also known by one skilled in the art that some amino acid substitutions, additions, and/or deletions may be made in a periplasmic targeting signal peptide while retaining the targeting function. Thus a functional periplasmic targeting signal peptide of use in the instant invention may be fully natural or modified.

The DNA sequence encoding a periplasmic targeting signal peptide is then readily identified by one skilled in the art and is used in the preparation of an isolated nucleic acid fragment encoding a fusion protein including the periplasmic targeting signal and an antimicrobial peptide.

Fusion Protein

The fusion proteins of the present invention comprise a periplasmic targeting signal (PerS) and one or more AMPs, which can be written as PerS-C-$(AMP)_n$ where C is a cleavage site and n is an integer from 1 to about 25. The cleavage site is located between the periplasmic targeting signal and the AMP to allow separation of these peptides. $(AMP)_n$ represents one, or a concatemer of AMP sequences. A concatemer of AMP sequences may be multiple tandem copies of the same AMP sequence, or it may include more than one AMP sequence. Examples of PerS-C-$(AMP)_n$ sequences where N=1 are OmpA/PerS-DP-16KGLG1 (SEQ ID NO:4) and GeneIII/PerS-DP-16KGLG1 (SEQ ID NO:5), where DP is the cleavage site aspartic acid-proline described below. When a concatemer of AMP sequences is included, it is preferred that the fusion protein has additional cleavage sites located between each set of two AMP encoding sequences, written as PerS-$(C\text{-}AMP)_n$.

The cleavage site is any site that can be used in separating the PerS and the first AMP, as well as separating individual AMPs, from each other. Any cleavage site making use of any method for protein cleavage may be used. Methods that have been successfully used and are well known to one skilled in the art include both enzymatic and chemical cleavage. Protease cleavage methods include thrombin (J. Y. Chang, European Journal of Biochemistry, Vol. 151, 217-224 (1985)), factor Xa protease (U.S. Pat. No. 5,589,364) and other endo peptidases, such as trypsin; the fusion genes encoding the fusion proteins can be synthesized to include a cleavage site for one of these proteases between the PerS peptide and the AMP comprising the fusion protein. Chemical methods include cleavage with cyanogen bromide at methionine residues (K. L. Piers, et al., Gene, Vol. 134 (1993)), dilute acid cleavage at aspartyl-prolyl bonds (H. Gram, et al., Bio/Technology, Vol. 12, 1017-1023 (1994)), and hydroxylamine cleavage at asparagine-glycine bonds at pH 9 (Moks, Bio/Technology, Vol. 5, 379-382 (1987)). Cyanogen bromide, for example, cleaves at methionine residues, and thus to utilize this mechanism of cleavage the fusion protein must have a methionine between the PerS peptide and the AMP comprising the fusion protein, and no methionine where cleavage is not desired. Accordingly, the fusion gene must be generated to include the appropriate nucleotide sequence encoding methionine between the PerS peptide and the AMP comprising the fusion protein. Similar strategies must be utilized for other chemical cleavage mechanisms. Strategies for the generation of fusion protein encoding genes and methods for cleaving fusion proteins are well known in the art, and are described, for example, in Current Protocols in Protein Science (1995), John Wiley & Sons, Unit 5. Another system for fusion and cleavage is the intein/chitin binding domain system (S. Chong, et al., Gene, Vol. 192, 271-281 (1997)). This system makes use of the self cleaving properties of intein proteins. Particularly useful in the instant invention is cleavage at an acid labile site, specifically at an aspartyl-prolyl (represented as DP, the one letter abbreviations for the amino acids) bond.

The isolated nucleic acid fragment-encoding a fusion protein including a periplasmic targeting signal and an antimicrobial peptide is constructed such that the expressed fusion protein contains a site for cleavage by a protease or a chemical on the N-terminal end of the most 5' antimicrobial peptide sequence, and optionally a cleavage site on the N-terminal end of each antimicrobial peptide sequence when multiple AMPs are present. "On the N-terminal end" refers to one or more amino acids encoded by a nucleotide sequence that is upstream of the 5' end of the sequence encoding the AMP.

The fusion protein may additionally include a tag that is a sequence of amino acids preferably located at the C-terminus. A tag is generally used to aid in tracking the associated protein or peptide or in purification. Particularly useful is a tag comprised of six histidine amino acids, called 6His, which is readily assayed using a commercially available antibody (sources include Novagen, Qiagen, and Invitrogen). Examples of fusion proteins with a 6His tag on the C-terminus are OmpA targeting signal-16KGLG1-6His (SEQ ID NO:6) and GeneIII targeting signal-16KGLG1-6His (SEQ ID NO:7), Fusion Protein Encoding Sequences The instant invention provides an isolated nucleic acid fragment encoding a fusion protein comprising a periplasmic targeting signal and at least one antimicrobial peptide. DNA sequences encoding AMPs of the invention may be sequences found in nature such as those encoding cathelicidins, magainins, cecropins and other natural peptides having similar properties. In addition, DNA sequences encoding AMPs may be deduced from the amino acid sequence using back-translation. Back-translated sequences may include differences from natural sequences such as codon changes providing optimal codons for gene expression in a particular host cell, as is well known by one skilled in the art. DNA sequences encoding non-natural antimicrobial peptides are generally ascertained by back-translation. For example, a DNA sequence encoding the non-natural AMP 16KGLG1 (SEQ ID NO:1) is shown in SEQ ID NO:8. A DNA fragment encoding an AMP that is used in a fusion protein encoding isolated nucleic acid fragment may be obtained using any method such as isolation from nature, chemical synthesis, or amplification such as by using PCR (Mullis, et al., U.S. Pat. No. 4,683,202). Methods of PCR primer design are common and well known in the art (Thein and Wallace, "The Use of Oligonucleotide as Specific Hybridization Probes in the Diagnosis of Genetic Disorders", In, Human Genetic Diseases: A Practical Approach, K. E. Davis, Ed., (1986) pp. 33-50 IRL Press, Herndon, Va.; Rychlik, W. In, Methods in Molecular Biology, B. A. White, Ed., (1993) Vol. 15, pp. 31-39; PCR Protocols: Current Methods and Applications, Humana Press, Inc., Totowa, N.J.; The Polymerase Chain Reaction (1994) Mullis, K. B., Ferre, F., and R. A. Gibbs (editors), Birkhaeuser, Boston). The desired DNA fragments may also be prepared using overlapping PCR primers, which are primers containing common sequences of contiguous nucleotides; the overlapping sequences may be from about 15 to about 18 nucleotides in length; the primers are generally between 30 and 60 bases in length. Methods for using overlapping primers to synthesize genes can be found in *PCR Protocols: Current Methods and Applications* (Humana Press, Inc., Totowa, N.J.).

DNA sequences encoding periplasmic targeting signals of the invention may be the natural coding sequences present in the genes from which they are derived. Additionally, the encoding sequence may be back-translated using the amino acid sequence of the periplasmic targeting signal, optionally using optimized codons. For example, a DNA sequence encoding an OmpA periplasmic targeting signal sequence is given as SEQ ID. NO:9 and a DNA sequence encoding a GeneIII periplasmic targeting signal sequence is given as SEQ ID NO:10. A DNA fragment encoding a periplasmic targeting signal that is used in a fusion protein encoding isolated nucleic acid fragment may be obtained using any method such as isolation from nature, chemical synthesis, or amplification such as by using PCR (Mullis, et al., U.S. Pat. No. 4,683,202). PCR methods described above may be used to produce the desired isolated nucleic acid fragment encoding a periplasmic targeting signal alone, or an isolated nucleic acid fragment encoding the combination of the periplasmic targeting signal and the at least one AMP. If an isolated nucleic acid fragment encoding the AMP and one encoding the periplasmic targeting signal are produced separately, these may be joined by cloning methods well known to one skilled in the art.

In addition, the desired cleavage site is included in the isolated nucleic acid fragment encoding the fusion protein by including the sequence encoding the cleavage site at the 5' end of the AMP encoding DNA fragment, at the 3' end of the periplasmic targeting signal encoding fragment, in between these two encoding regions if preparing them in one fragment, or by other cloning methods known to one skilled in the art. A DNA sequence encoding the preferred aspartic acid-proline (DP) cleavage site is GACCCG, which is given in positions 64 to 69 of SEQ ID NO:13.

A sequence encoding a tag such as the 6His tag may be incorporated, if desired, into the fusion protein encoding sequence by methods described above. A DNA sequence encoding a 6His tag is CACCATCATCACCATCAC, which is given in positions 112 to 129 of SEQ ID NO:11. Also, sequences may be added that provide restriction sites, hybridization extensions, or other features used in cloning to prepare the desired fusion protein encoding constructions.

Examples of DNA sequences encoding fusion proteins of the invention are those encoding:

a) OmpA signal sequence -DP-16KGLG1: SEQ ID NO:13 b) GeneIII signal sequence-DP-16KGLG1: SEQ ID NO:14

Promoters and Termination Control Regions

An isolated nucleic acid sequence of the invention comprising DNA sequences encoding a periplasmic targeting signal, at least one AMP, and preferably at least one cleavage site is operably linked to suitable regulatory sequences in a chimeric gene construct for expression in a host cell. Especially useful are regulatory sequences that direct high level expression of foreign proteins. Regulatory sequences include promoters and terminators for transcription, as well as translation control regions. Promoters, which are useful to drive expression of the instant coding regions in the desired host cell, are numerous and familiar to those skilled in the art. Virtually any inducible or constitutive promoter capable of driving these genes in Gram negative bacteria, and particularly in *E. coli*, is suitable for the present invention including, but not limited to: lac, ara, tet, trp, lambda $P_L$, lambda $P_R$, T7, tac, trc, malE (maltose binding protein promoter) and derivatives thereof. Preferred promoters are inducible promoters. Particularly useful is the $P_L$ promoter system of pLEX (U.S. Pat. No. 4,874,702).

Termination control regions may also be derived from various genes native to the preferred hosts. Optionally, a termination site may be unnecessary; however, it is most preferred if included.

Vectors

Vectors useful for the transformation of an isolated DNA fragment encoding a fusion protein of the instant invention into suitable host cells are well known in the art. Typically the vector contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Vectors may also be used which promote the integration of the chimeric gene encoding a fusion protein of the invention into the host cell genome. Such vectors may be for random integration, site-directed integration, or for homologous recombination. A vector may have features allowing single cross-over or double-crossover types of homologous recombination. One or multiple copies of a chimeric AMP encoding gene may be integrated into a host cell genome.

Microbial Recombinant Expression

The genes encoding the fusion proteins of the instant invention may be introduced into heterologous host cells, particularly in the cells of microbial hosts, for expression. Thus the instant invention provides a transformed host cell comprising an isolated nucleic acid fragment under the control of suitable regulatory sequences, the isolated nucleic acid fragment encoding a fusion protein, the fusion protein comprising a periplasmic targeting signal and at least one antimicrobial peptide.

Host cells preferred for expression of the instant fusion proteins are microbial hosts that can be found within the family of Gram negative bacteria, including enteric bacteria. Examples of suitable host strains include, but are not limited to, the Gram negative, aerobic or facultatively anaerobic rods or cocci, such as members of the genera *Escherichia, Pseudomonas, Klebsiella, Salmonella, Caulobacter, Methylomonas, Acetobacter, Achromobacter, Acinetobacter, Aeromonas, Agrobacterium, Alcaligenes, Azotobacter, Burkholderia, Citrobacter, Comamonas, Enterobacter, Erwinia, Rhizobium, Vibrio* and *Xanthomonas*. Most preferred is *E. coli*. Host cells also include Gram negative bacteria that are protease deficient. For example Williams, et al. (U.S. Pat. No. 5,589,364) describe a method for fusion of an AMP to the maltose binding protein as a fusion partner and increasing the effective level of production by expressing this protein in a protease deficient host.

Large scale microbial growth and fusion protein expression may utilize a wide range of simple or complex carbohydrates, organic acids or alcohols, and saturated hydrocarbons such as methane. Fusion protein encoding gene expression may be regulated, repressed or depressed by specific growth conditions, which may include the form and amount of nitrogen, phosphorous, sulfur, oxygen, carbon or any trace micronutrient including small inorganic ions. In addition, the regulation of AMP genes may be achieved by the presence or absence of specific regulatory molecules that are added to the culture and are not typically considered nutrient or energy sources.

Protein Purification

The fusion proteins of the instant invention can be purified by any of the standard methods practiced in the art to separate proteins based on size, charge, ligand specificity or hydrophobicity. These methods include size exclusion, ion exchange, hydrophobic interaction, reversed phase and affinity chromatography. Affinity chromatography may utilize antibodies, or may, for example, take advantage of metal chelate techniques such as utilizing nickel-containing resin to purify His-tagged proteins (in which case a region encoding about six histidines would be added to the fusion protein coding region). Methods for the purification of recombinantly expressed proteins are described in detail in Guide to Protein Purification (Deutscher (ed.), 1990, Methods in Enzymology, Vol. 182, Academic Press, San Diego, Calif.) or Current Protocols in Protein Science, supra (Units 6, 8 and 9). The choice of purification method depends not only on the protein properties, but also on the quantity to be purified. Preferred is purification based on differential precipitation, which is facilitated by the presence of the hydrophobic periplasmic targeting signal. Specifically, purification is by retention of urea solubilized fusion protein on silica based reverse phase packing in batch mode, followed by elution with greater than about 50% acetonitrile.

Separation of Periplasmic Targeting Signal and AMPs

Fusion proteins of the invention are cleaved to unlink the periplasmic targeting signal and the one or more linked AMP(s). Cleavage is by a method known to one skilled in the art at a cleavage site engineered between the periplasmic targeting signal and the adjacent AMP, or between multiple AMPs, as described previously. When using the preferred aspartic acid-proline (DP) cleavage site, cleavage takes place under acidic conditions. For example, the sample may be brought to an acidic pH and heated. Following cleavage the aspartic acid residue remains linked to the C-terminus of the upstream peptide and the proline residue remains linked to the N-terminus of the downstream peptide. For example, the OmpA targeting signal sequence-DP-16KGLG1 fusion protein is cleaved to produce OmpAD (SEQ ID NO:15) and P16KGLG1 (SEQ ID NO:16) peptides. The periplasmic targeting signal peptides are then separated from the AMPs to provide a purified preparation of AMPs to be used in antimicrobial applications. The AMPs prepared in this manner are derived from the fusion proteins.

Applicants have found that due to the hydrophobic nature of the periplasmic targeting signal peptide, separation of the cleaved peptides can be achieved by differential hydrophobic precipitation. Any method able to separate peptides of differing hydrophobicity may be used. Of particular use is a method relying on the property that the hydrophobic targeting signal peptides preferentially precipitate in acidic solutions. The hydrophobic periplasmic targeting signal peptide precipitates, even over a wide range of pH values, while the antimicrobial peptide remains soluble. The difference in precipitation properties of the two peptides increases as the pH is reduced, due to reduction in periplasmic targeting signal peptide solubility. Therefore using a neutral to acid pH provides better separation. Preferred is separation at a pH between about 1 and about 6. More preferred is separation at a pH of between about 1 and about 4. The mixture of periplasmic targeting signal peptides and AMPs may be incubated in an acidic solution for a period of time to allow maximal precipitation of the hydrophobic periplasmic targeting signal peptides.

Industrial Production

Production fermentation or "scale up" fermentation in this invention describes greater than 10 L aerobic batch fermentation, and usually 200 L or greater. Where commercial production of AMPs derived from fusion proteins of the instant invention is desired, a variety of culture methodologies may be applied. For example, large-scale production from a recombinant microbial host may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.,* 36, 227, (1992), herein incorporated by reference.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. The carbon substrates may also comprise, for example, alcohols, organic acids, proteins or hydrolyzed proteins, or amino acids. Additionally the carbon substrate may also be one-carbon substrates such as carbon dioxide or methane for which metabolic conversion into key biochemical intermediates has been demonstrated. In addition to one and two carbon substrates, methylotrophic organisms are also known to utilize a number of other carbon containing compounds such as methylamine and glucosamine, as well as methanol and a variety of amino acids for metabolic activity. Hence, it is contemplated that the source of carbon utilized in the present invention may encompass a wide variety of carbon containing substrates and will only be limited by the choice of organism.

Commercial production of fusion proteins may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Applications

The instant invention provides a method for cost-effectively producing and purifying linear, α-helical AMPs. The instant invention further provides a method for producing and purifying AMPs that are toxic to host cells or cannot be expressed by host cells due to proteolysis.

Peptides produced by the process of the present invention are effective as antimicrobials and can be employed to kill, inhibit the growth of, or prevent the growth of microorganisms such as Gram-positive bacteria, Gram-negative bacteria, viruses, and fungi. The peptides produced by the process of the present invention are effective in antimicrobial compositions for use against disease-causing organisms in humans, animals, aquatic and avian species, and plants. The peptides and compositions thereof may be used in pharmaceutical preparations as systemic or topical antibiotics for infectious disease applications. The peptides and compositions thereof can also be used as preservatives or sterilants for articles susceptible to microbial contamination. The peptides of the present invention and compositions thereof can be administered to a target cell or host by direct or indirect application. For example, the peptide may be administered topically, systemically or as a coating. The peptides of the present invention and compositions thereof may also be bound to or incorporated into substrates to provide antimicrobial substrates to reduce or inhibit microbial contamination of the substrate. The present invention also provides articles, or antimicrobial articles, comprising the antimicrobial peptides of the invention.

In the articles of the invention, the antimicrobial peptides of the invention may be applied to different substrates, thereby providing antimicrobial properties to the substrate. Substrates suitable for the present invention include polymers selected from the group consisting of latex, polyvinyl chloride, polyimide, polyesters, polyethylene, polypropylene, polyamides, polyacrylates, polyolefins, polysaccharides, polyurethane, polysulfone, polyethersulfone, polycarbonate, fluoropolymers, cellulosics, synthetic rubber, silk, silicone, and mixtures or blends thereof. Additional polymer substrates are also functionalized polymer substrates comprising the aforementioned polymers and that additionally contain, or may be functionalized to contain, active groups with which peptides may react, and which allow for immobilization of the peptides. Examples of active groups include, but are not limited to: acrylic acid, acetal, hydroxyl, amines, epoxides, carboxylates, anhydrides, isocyanates, thioisocyanates, azides, aldehydes, halides, acyl halides, aryl halides and ketones at 1 to 50% by weight of the polymer.

Various methods of protein or peptide immobilization are described in Protein Immobilization (Richard F. Taylor (ed.), Marcel Dekker, New York, 1991).

Substrates suitable for the present invention also include ceramics, glass, metal, metal oxides, and composites comprised of ceramics, glass, metals or metal oxides plus polymers as described above. Suitable metals include steel, stainless steel, aluminum, copper, titanium, alloys thereof, and combinations thereof.

Additional substrates suitable for the present invention include artificial (or synthetic) marble. Artificial marbles encompass cultured marble, onyx and solid surface materials typically comprising a resin matrix, the resin matrix comprising one or more fillers. Typically, cultured marble is made of a gel coating of unfilled unsaturated polyester on a substrate of a filled unsaturated polyester. The filler may be calcium carbonate or a similar material. Onyx typically consists of a gel coat of unfilled unsaturated polyester on a substrate of filled unsaturated polyester. The filler in this case is typically alumina trihydrate (ATH). Solid surface materials are typically filled resin materials and, unlike cultured marble or onyx, do not have a gel coat. Corian® material available from E. I. du Pont de Nemours and Company (DuPont), Wilmington, Del., is a solid surface material comprising an acrylic matrix filled with ATH. An additional solid surface DuPont material, known by the brand name Zodiaq®, is described as an engineered stone or artificial granite. Such materials are made from an unsaturated polyester matrix filled with quartz.

The articles of the present invention have antimicrobial peptides of the invention bound to or incorporated into a substrate, thereby rendering them antimicrobial articles. The use of antimicrobial peptides for rendering substrates antimicrobial provides many advantages to traditional molecules in that peptides exhibit rapid biocidal activity, broad spectrum activity, reduced environmental toxicity and a reduced likelihood of causing organisms to become resistant. Peptides can be bound to a substrate either physicochemically, or covalently. Physicochemical binding of peptides to the substrate may occur by any one or combinations of the following forces: electrostatic, hydrogen bonding, and Van der Waals. Alternatively, peptides may be bound to the substrate surface by a covalent bond. Additionally, antimicrobial peptides of the present invention can be incorporated into the polymer by mixing with the polymer, for example by dissolving the peptide and the polymer in a common solvent and casting or molding the peptide:polymer mixture into an article.

In one embodiment, the antimicrobial peptide is bound to the substrate by coating a substrate polymer with an aqueous or non-aqueous solution of the peptide, wherein the peptide is at concentration ranging from about 0.001 to about 20 weight percent. The peptide is contacted with the substrate polymer, and the peptide and polymer may be shaken at temperatures ranging from about 10° C. to about 100° C. for a period of time ranging from about 10 min to about 96 hrs. Preferably the peptide and polymer are shaken at a temperature of from about 25° C. to about 80° C. for a period of time ranging from about 1 hr to about 24 hrs.

In another embodiment, the substrate polymer is primed to generate active groups that will bind to the antimicrobial peptide. Surface modification of the polymer may be achieved by a variety of techniques well known in the art including: oxidation, reduction, hydrolysis, plasma, and irradiation. Substrate polymers containing acid or base hydrolyzable groups such as polyesters, polyamides, and polyurethanes may be treated with acid or base first. Subsequently, the hydrolyzed polymer is brought into contact with an aqueous or non-aqueous solution of from about 0.001 to about 20 weight percent of the antimicrobial peptide. The peptide and the polymer may be shaken at temperatures ranging from about 10° C. to about 100° C. for a period of time ranging from about 10 min to about 96 hrs. Preferably the peptide and polymer are shaken at a temperature of from about 25° C. to about 80° C. for a period of time ranging from about 1 hr to about 24 hrs.

In another embodiment, a commercial substrate polymer containing 1-50% active groups is brought into contact with an aqueous or non-aqueous solution comprising from about 0.001 to about 20 weight percent of the antimicrobial peptide.

After treatment with the antimicrobial peptide, the article may be washed, preferably with deionized water. Optionally, the article may then be dried via methods known in the art. Such methods include ambient air drying, oven drying, and air forced drying. In one preferred embodiment, the article is dried at about 50° C. to about 120° C., more preferably at about 50° C. to about 100° C., for about 15 min to about 24 hrs.

Articles comprising the polymer substrate of the present invention may be in the form of or comprise an extrudate, film, membrance, laminate, knit fabric, woven fabric, nonwoven fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, or spinning.

The preferred articles of the present invention provide multiple uses, since many articles benefit from a reduction in microbial growth and a wide variety of substrates are included in the present invention. The following are examples of articles wherein it is desirable to reduce microbial growth in or on the article in the end-use for which the particular article is commonly used.

The articles of the invention include packaging for food, personal care (health and hygiene) items, and cosmetics. By "packaging" is meant either an entire package or a component of a package. Examples of packaging components include but are not limited to packaging film, liners, absorbent pads for meat packaging, tray/container assemblies, caps, adhesives, lids, and applicators. The package may be in any form appropriate for the particular application, such as a can, box, bottle, jar, bag, cosmetics package, or closed-ended tube. The packaging may be fashioned by any means known in the art, such as by extrusion, coextrusion, thermoforming, injection molding, lamination, or blow molding.

Some specific examples of packaging include, but are not limited to bottles, tips, applicators, and caps for prescription and non-prescription capsules and pills; solutions, creams, lotions, powders, shampoos, conditioners, deodorants, antiperspirants, and suspensions for eye, ear, nose, throat, vaginal, urinary tract, rectal, skin, and hair contact; lip product packaging, and caps.

Examples of applicators include lipstick, chapstick, and gloss; packages and applicators for eye cosmetics, such as mascara, eyeliner, shadow, dusting powder, bath powder, blusher, foundation and creams. These applicators are used to apply substances onto the various surfaces of the body and reduction of bacterial growth will be beneficial in such applications.

Other forms of packaging components included in the present invention include drink bottle necks, replaceable caps, non-replaceable caps, and dispensing systems; food and beverage delivery systems; baby bottle nipples and caps; and pacifiers. Where a liquid, solution or suspension is intended to be applied, the package may be fashioned for application in a form for dispensing discrete drops or for spraying of droplets. The invention will also find use in pharmaceutical applications fashioned as inhalers.

Examples of end-use applications, other than packaging, in the area of food handling and processing that benefit from antimicrobial functionality and wherein microbial growth is reduced in the particular end-use of the consumer are coatings for components of food handling and processing equipment, such as temporary or permanent food preparation surfaces; conveyer belt assemblies and their components; equipment for mixing, grinding, crushing, rolling, pelletizing, and extruding and components thereof; heat exchangers and their components; and machines for food cutting and slicing and components thereof. Where the surface of such equipment components is metal, the metal could be coated directly, or a coating of a polymer or functionalized polymer could first be applied to the metal surface. Alternatively, a film of such a polymer or functionalized polymer could be coated with an antimicrobial peptide of the invention and then applied to the equipment surface. Additional articles of the invention include foods and seeds.

Articles of the present invention can also be used in or as items of apparel, such as a swimsuit, undergarment, shoe component (for example, a woven or nonwoven shoe liner or insert), protective sports pad, and child's garment. Articles of the invention also include protective medical garments or barrier materials, such as gowns, masks, gloves, slippers, booties, head coverings or drapes.

Articles of the present invention can also be used in or as medical materials, devices, or implants, such as bandages, adhesives, gauze strips, gauze pads, syringe holders, catheters such as central venous catheters and peripheral IV catheters, sutures, urinary catheter ostomy ports, orthopedic fixtures, orthopedic pins, pacemaker leads, defibrillator leads, ear canal shunts, vascular stents, cosmetic implants, ENT implants, staples, implantable pumps, hernia patches, plates, screws, blood bags, external blood pumps, fluid administration systems, heart-lung machines, dialysis equipment, artificial skin, artificial hearts, ventricular assist devices, hearing aids, vascular grafts, pacemaker components, hip implants, knee implants, and dental implants.

In the hygiene area, articles of the present invention include personal hygiene garments such as diapers, incontinence pads, sanitary napkins, sports pads, tampons and their applicators; and health care materials such as antimicrobial wipes, baby wipes, personal cleansing wipes, cosmetic wipes, diapers, medicated wipes or pads (for example, medicated wipes or pads that contain an antibiotic, a medication to treat acne, a medication to treat hemorrhoids, an anti-itch medication, an anti-inflammatory medication, or an antiseptic).

Articles of the present invention also include items intended for oral contact, such as a baby bottle nipple, pacifier, orthodontic appliance or elastic bands for same, denture material, cup, drinking glass, toothbrush, or teething toy.

Additional child-oriented articles that benefit through comprising the polymer substrate of the present invention include baby bottles, baby books, plastic scissors, toys, diaper pails, and a container to hold cleansing wipes.

Household articles of the present invention include telephones and cellular phones; fiberfill, bedding, bed linens, window treatments, carpet, flooring components, foam padding such as mat and rug backings, upholstery components (including foam padding), nonwoven dryer sheets, laundry softener containing sheets, automotive wipes, household cleaning wipes, counter wipes, shower curtains, shower curtain liners, towels, washcloths, dust cloths, mops, table cloths, walls, and counter surfaces.

The current invention is also useful in reducing or preventing biofilm growth on the surface of separation membranes (for example, pervaporation, dialysis, reverse osmosis, ultrafiltration, and microfiltration membranes) comprised of polymer substrates of the invention.

In order to impart antimicrobial functionality to the products listed, the product can be treated with an antimicrobial peptide of the invention before it is manufactured, or after, or at any time during manufacture of the product. For example, in making an antimicrobial shower curtain, an antimicrobial peptide of the invention may be bound to or incorporated into the polymer substrate, followed by fashioning a shower curtain from the treated material. Alternatively, treatment of the polymer substrate with an antimicrobial peptide of the invention may be performed after the substrate is made into a shower curtain. It is believed that the antimicrobial properties of the material will not change significantly.

Antimicrobial substrates or articles prepared by methods of the invention exhibit antimicrobial functionality, wherein microbes are killed, or microbial growth is reduced or prevented. Antimicrobial activity of the antimcrobial substrate or article can be determined by using any of a number of methods well known in the art, such as the antimicrobial assay described in the General Methods of the present invention. Additional methods for determining antimicrobial activity are discussed in Tenover et al. (eds.), Manual of Clinical Microbiology, 7$^{th}$ Edition, Section VIII, 1999, American Society for Microbiology, Washington, D.C.

The present invention provides antimicrobial compositions comprising at least one antimicrobial peptide prepared from a fusion protein comprising a periplasmic targeting signal and at least one AMP. The antimicrobial peptide comprises from about 0.00001% to about 20% by weight of the composition. In another embodiment of the invention the antimicrobial peptide comprises from about 0.0001% to about 10% by weight of the composition. In still another embodiment of the invention the antimicrobial peptide comprises from about 0.0001% to about 5% by weight of the composition.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Procedures for ligations and transformations are well known in the art. Techniques suitable for use in the following examples may be found in Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989).

Materials and methods suitable for the maintenance and growth of bacterial cultures are well known in the art. Techniques suitable for use in the following examples may be found as set out in *Current Protocols in Molecular Biology*, (F. Ausubel, R. Brent, R. E. Kingston, D. D. Moore, J. G. Seidman, J. A. Smith, K. Struhl, [editors], Wiley and Sons, Inc, New York, N.Y., [2002]). All reagents, restriction enzymes and materials used for the growth and maintenance of bacterial cells were obtained from DIFCO Laboratories (Detroit, Mich.), GIBCO/BRL (Gaithersburg, Md.), or Sigma Chemical Company (St. Louis, Mo.) unless otherwise specified.

Materials and methods suitable for gel electrophoresis and Western blotting may be found in *Current Protocols in Protein Science*, (J. E. Coligan, et al., [editors], Wiley and Sons, Inc, New York, N.Y., [2002]). Reagents were obtained from Invitrogen (Carlsbad, Calif.), Biorad (Hercules, Calif.) or Pierce Chemicals (Rockford, Ill.) unless otherwise indicated.

The meaning of abbreviations is as follows: "hr" means hour(s), "min" or "min." means minute(s), "day" means day(s), "msec" means millisecond(s), "ml" means milliliters, "L" means liters, "μl" means microliters, "mM" means millimolar, "μM" means micromolar, "pmol: means picomol(s), "°" means degrees Centigrade, "RT" means room temperature, "bp" means base pair, "bps" means base pairs, "kDa" means kilodaltons, "kV" means kilovolt(s), "μF" means microfarrad.

Bacterial Strains and Plasmids:

The pLEX expression system marketed by Invitrogen (Carlsbad, Calif.) is subject to U.S. Pat. No. 4,874,702, Canadian Patent No. 1,207,251; and European Patent No. 41,767. The sequence for plasmid pLEX is available from Invitrogen. pLEX carries the $P_L$ promoter for high-level expression of recombinant protein, lambda cII ribosome binding site and initiation ATG for efficient translation of recombinant protein, the *E. coli* aspA transcription terminator, an ampicillin resistance marker, the ColE1 origin of replication and a polylinker region for cloning of gene inserts in appropriate juxtaposition to the $P_L$ promoter. *E. coli* strain GI724 has genotype F-, lambda-, lacI$^q$, lacPL8, ampC::$P_{trp}$cI, mcrA, mcrB, INV(rnnD-rnnE). This strain contains the cI repressor under control of the trp promoter (Mieschendahl, et al., Bio/Technology, 4, 802-806, (1986)). In the PLEX expression system, in the absence of tryptophan, the lambda cI repressor is expressed from the trp promoter and prevents transcription of the gene of interest by binding to the $P_L$ operator. When tryptophan is added, the repressor promoter (trp) is blocked. When the existing cI repressor falls off the $P_L$ operator, there is no PL repressor to replace it and the gene of interest is expressed. *E. coli* strain ATCC No. 25922 is a wild type strain recommended for standard *E. coli* static bioassays.

Standard Protocols

*E. coli* Static Bioassay:

*E. coli* 25922 was grown in Trypticase Soy Broth (TSB; Difco) overnight from a single colony. Log phase *E. coli* cells were diluted to $2\times10^5$ CFU/ml in TSB. Experimental samples were added to the first row of a 96 well plate in duplicate and serially diluted with TSB across the plate. Ampicillin was used as the negative growth control at a starting concentration of 1 mg/ml. TSB was used as a positive growth control. Each well then received 0.1 ml of diluted *E. coli* for a final inoculation of $10^5$ CFU/ml per well. Bioassay plates were incubated for 18 hr at 37° C. and then scored for growth or no growth by visual inspection ("cloudiness") of each well. TSB is composed of 1.7% pancreatic digest of casein, 0.3% papaic digest of soybean meal, 0.5% NaCl, 0.25% dipotassium phosphate, and 0.25% dextrose.

HPLC Analysis:

Antimicrobial peptides and fusion proteins expressed in *E. coli* cells were visualized by RP-HPLC as follows. Peptides were separated using an analytical Varian Dynamax Microsorb C18 column (300 Angstrom pore size, 10 micron particle size, 250 mm length×4.6 mm ID) on a Varian (Walnut Creek, Calif.) ProStar HPLC system. Solvent A consisted of 95% water, 5% acetonitrile, 0.1% trifluoroacetic acid (TFA) and Solvent B consisted of 95% acetonitrile, 5% water, 0.1% TFA. The gradient was 10% B to 30% B over 10 min. then 30% B to 70% B over 50 mins. The flow rate was 1 ml/min. Peptides were detected using a photodiode array detector at 214 nm. The target molecule P16KGLG1 (SEQ ID NO:16) was identified as a peak at 22.4 mins (43% B). Standard curves for peak area versus known quantities of synthetic purified or purified recombinant peptides were generated. The quantity of peptide in samples from purification steps was extrapolated from these curves.

Western Blot Analyses:

The 16KGLG1 (SEQ ID NO:1) peptide was synthesized leaving a free COOH terminus. Antibodies were produced in rabbits by Covance (Denver, Pa.). Prior to conjugation, 16KGLG1 had free amines blocked with citraconic anhydride. 16KGLG1 (G1) was conjugated to Keyhole Limpet Hemocyanin (KLH) in an 800 to 1 molar excess ratio (approximate 1:1 weight ratio) for increased immunogenicity. The conjugate was dialyzed against 100 mM potassium acetate, pH 4. This allowed concurrent deprotection of the citraconic anhydride and removal of excess 16KGLG1. A final dialysis with PBS was done prior to immunization of rabbits. Numerous attempts to induce antibodies against the G1 peptide were unsuccessful. The following protocol was used in successful antibody production.

The immunization schedule for Elite Rabbits was as follows:

| | |
|---|---|
| Day 1 | 500 ug KLH-G1 + Freund's Complete Adjuvant (equal volume, 0.6 ml) intradermal into back, multiple sites |
| Day 22 | 250 ug KLH-G1 + Freund's Incomplete Adjuvant (FIA, equal volume, 1 ml) Sub Cutaneous nodal area |
| Day 42 | 250 ug KLH-G1 + FIA (equal volume, 0.6 ml) Subcutaneous nodal area (SCNO) |
| Day 52 | 1st bleed |
| Day 63 | 250 ug KLH-G1 + FIA (equal volume, 1 ml) SC + intramuscular (IM) NO |

-continued

| | |
|---|---|
| Day 73 | 2nd bleed |
| Day 84 | 250 ug KLH-G1 + FIA (equal volume 1 ml) SCNO |
| Day 94 | 3rd bleed |
| Day 105 | 250 ug KLH-G1 + FIA (equal volume 0.5 ml) NO |
| Day 115 | 4th bleed |
| Day 126 | 250 ug KLH-G1 + FIA (equal volume 1 ml) SCNO |
| Day 136 | 5th bleed |
| Day 143 | final bleed |

This final bleed was diluted 1:100 and used in all Examples.

Gel Electrophoresis:

Protein samples were prepared by addition of NuPage Sample Buffer dye (Invitrogen Life Technologies, Carlsbad, Calif.) (diluted to 1× in the sample), then heated at 70° C. for 10 min prior to loading on the gel. Protein samples (10-20 μl) were loaded onto NuPage Bis-Tris 4-12% gradient gels (Invitrogen). Proteins were separated by electrophoresis in MES SDS buffer (50 mM 2-(N-morpholino) ethane sulfonic acid, 50 mM Tris, 3.47 mM SDS, 1 mM EDTA, pH 7.3) at 100 V for 1.5 hr or until the Phenol Red dye front was at the bottom of the gel.

Alternatively, proteins were separated on 10-20% Tris-Tricine gradient gels (Invitrogen) using 0.2M Tris pH9.0 as the cathode buffer and Tricine buffer as the anode buffer. Gels were electrophoresed at 125 Volt for 1.5 hrs.

Western Blotting:

Proteins in the gels were transferred to 0.2 micron nitrocellulose membranes at 30 V for 2 hr in NuPage Transfer buffer (25 mM Bicine, 25 mM Bis-Tris, 1 mM EDTA, 50 μM chlorobutanol with 20% methanol, pH 7.2).

Visualization:

Transferred peptides were visualized using MemCode (Pierce Chemicals: Rockford, Ill.) stain on nitrocellulose to assure transfer. The blot was blocked with Super Block (Pierce Chemicals; Rockford, Ill.) +0.05% Tween 20 overnight at 4° C. The blot was then incubated with anti-16KGLG1 primary antibody diluted 1:100 in Super Block+0.05% Tween 20 for 1 hr with shaking at RT. The blot was washed thoroughly with Tris Buffered Saline+0.05% Tween 20 (TBST). Goat anti-Rabbit Secondary antibody conjugated to Horse Radish Peroxidase was diluted 1:100,000, added to the blot, and incubated for 1 hr with shaking at RT. The blot was washed thoroughly with TBST. The blot was incubated in Super Signal West Pico Rabbit IgG detection chemiluminescent substrate (Pierce Chemicals) (equal volumes of luminol/enhancer and stable peroxide buffer) for 5 min. Digital images, generated on a Kodak imager (Model #440CF, Kodak; Rochester, N.Y.) were used to quantitate the amount of 16KGLG1 (SEQ ID NO:1) related peptides in samples.

Example 1

Construction of a Chimeric Gene Encoding a Fusion Protein of the Periplasmic Targeting Signal from OmpA with an Antimicrobial Peptide A DNA fragment containing the OmpA signal peptide coding sequence (SEQ ID NO:11) fused to the 16KGLG1 antimicrobial peptide coding sequence (SEQ ID NO:8) and a 6His coding sequence was synthesized in an annealing reaction using the oligonucleotide primers: SEQ ID NOs:17-22. For ligations, internal primers were 5' phosphorylated. One nmol of each primer was combined and heated to 90° C. for 5 min and allowed to cool slowly (in heat block) to RT in order to allow slow annealing of the overlap regions. When cool, 1× Ligase buffer and 20 units of ligase were added to the primer mix. The ligation mix was incubated overnight at 4° C.

PCR Amplification:

One μl of the ligation reaction was used in a PCR reaction with 25 pmol of each primer, SEQ ID NOs:23 and 24. The primers were reconstituted in $ddH_2O$ to a working concentration of 5 pmoles/μl. The PCR consisted of 10 pmoles of each of the primers, 1×Pfu polymerase buffer (Invitrogen), 0.4 mM dNTPs, and 2 units Pfu polymerase in a 50 μl reaction. A Perkin Elmer thermocycler GENEAMP PCR system 9700 (Perkin Elmer Applies Biosystems; Branchburg, Va.) was used to incubate the reaction as follows: 5 cycles, each with melting at 94° C. for 30 seconds, annealing at 72° C. for 30 sec, 45 sec extension at 72° C., then followed with 25 cycles consisting of melting at 94° C. for 30 sec, annealing at 74° C. for 30 sec, 45 sec extension at 72° C., then followed by one final extension for 5 min at 72° C. The resulting fragment size and purity was determined by electrophoresis on a 4% Egel (Invitrogen, Carlsbad, Calif.) agarose gel. The gel showed a major band corresponding to a fragment of 149 bp (SEQ ID NO:25), matching the expected product which contains SEQ ID NO:11 and terminal restriction sites with tails, provided in the primers, to allow restriction digestion.

Restriction Digests:

The PCR product was purified by PCRQuick (Qiagen) and digested with restriction enzyme BamHI by incubating 1 μg PCR fragment in 1× React 3 buffer, with 10 units of BamHI in a volume of 100 μat 37° C. for 4 hr. The digested fragment was ethanol precipitated, dried, and resuspended in $ddH_2O$. The fragment was then digested with NdeI by incubating the BamHI digested fragment in 1× React 2 buffer with 10 units of NdeI in a volume of 100 μl at 37° C. for 4 hr. The double digested fragment was isolated by ethanol precipitation, dried, and resuspended in $ddH_2O$.

The plasmid pLEX was digested with both NdeI and BamHI following a similar protocol as above. Cloning into the NdeI and BamHI sites in the polylinker region of pLEX results in gene insertion in appropriate juxtaposition to the $P_L$ promoter. After digestion, the plasmid was electrophoresed on a 1.5% agarose gel in Tris Borate EDTA buffer and the linear plasmid was gel purified using a SpinX column (Corning Inc, Corning, N.Y.).

Ligation:

The PCR product encoding the OmpA PerS-16KGLG1-6His (SEQ ID NO:6) was digested as described above to expose the designed flanking sequences that allowed directional cloning into the NdeI and BamHI restriction enzyme sites of the vector, pLEX. Ligation occurred when 60 ng of linearized plasmid was mixed with 60 ng of OmpA PerS-16KGLG1-6His insert and 0.5 units of T4 DNA ligase in 1× ligation buffer, with a final volume of 10 μl, and incubated at 4° C. for 18 hr. The resultant plasmid containing the PCR product insert operably linked for expression from the $P_L$ promoter was named pLH119.

Transformation:

Electro-competent GI724 cells were made by growing a single colony overnight at 37° C. in 5 ml of low salt LB broth. A 0.5% inoculum of the overnight culture was added to 500 ml of low salt LB in a 2 L baffle flask and incubated at 37° C. at 300 rpm until an $OD_{600}$ of 0.6-0.7 was reached. Chilled cells were pelleted by centrifugation then washed in 500 ml ice-cold $ddH_2O$. This process was repeated, with the pellet finally resuspended in 500 μl of ice-cold 10% glycerol and kept on ice until electroporation. Electroporation of the ligation mixture was performed in pre-chilled cuvettes (2 mm gap size) with a BioRad GenePulser set to 2.5 kV, 25 μF capacitance, and 200 ohms resistance, with a range of 4-5 msec pulse duration.

Electro-transformed cells were grown in SOC media (2% tryptone, 0.5% yeast extract, 10 mM NaCl, 2.5 mM KCl, 10 mM $MgCl_2$, 10 mM $MgSO_4$, 20 mM glucose) at 37° C. for 45 min then plated onto RM agar (RM formula: 1×M9 salts, 2% casamino acids, 1% glycerol, 1 mM $MgCl_2$, and 100 μg/ml ampicillin) for 24 hr at 30° C. for selection of transformants. Ampicillin resistant colonies were screened for the insertion of the OmpA PerS-16KGLG1-6His fusion coding sequence fragment in the pLEX plasmid by analysis of PCR product fragment length using the PCR amplification primers described above (SEQ ID NOs:23 and 24).

Sequence Analysis:

Isolates were sequenced by standard methodology using sequencing primers SEQ ID NOs:26 and 27. Sequence results indicated that the OmpA PerS-16KGLG1-6His encoding fragment was successfully cloned into the pLEX vector creating a chimeric gene for protein expression in *E. coli*.

Example 2

Construction of a Chimeric Gene Encoding a Fusion Protein of the Periplasmic Targeting Signal from GeneIII and an Antimicrobial Peptide A DNA fragment containing the GeneIII targeting signal sequence peptide (GeneIIISS) coding sequence (SEQ ID NO:10) fused to the 16KGLG1 antimicrobial peptide coding sequence (SEQ ID NO:8) and a 6His coding sequence was synthesized in a PCR amplification reaction using the following oligonucleotide primers: SEQ ID NOs:28-31. The primers were reconstituted in $ddH_2O$ to a working concentration of 5 pmoles/μl.

PCR Amplification:

The first round of PCR consisted of 10 pmoles of each of the primers (SEQ ID NOs:28-31), 1×Pfu polymerase buffer (Invitrogen), 0.4 mM dNTPs, and 2 units Pfu polymerase in a 50 μl reaction. A Perkin Elmer thermocycler GENEAMP PCR system 9700 (Perkin Elmer Applies Biosystems; Branchburg, Va.) was used to incubate the reaction as follows: two cycles of 94° C. melting for 30 sec followed by 46° C. annealing for 30 sec followed by 72° C. extension for 1 min, then 8 cycles of 94° C. melting for 30 sec followed by 46° C. annealing for 30 sec followed by 72° C. extension for 1 min, with a final extension at 72° C. for 2 min. For the second round of amplification, 5 μl of the first round amplification was used as template.

In the second round the use of short, end-sequence specific primers allowed amplification of the entire sequence. The reaction mix contained 20 pmoles of each primer, (SEQ ID NOs:32 and 33), 1×Pfu polymerase buffer, 1 mM dNTPs, and 4 units of Pfu polymerase in a 100 μl volume. The reaction was incubated for 5 cycles of: 94° C. melting for 30 sec followed by 70° C. annealing for 30 sec followed by 72° C. extension for 1 min; then 25 cycles of: 94° C. melting for 30 sec followed by 75° C. annealing for 30 sec followed by 72° C. extension for 1 min; with a final extension at 72° C. for 2 min. Resulting fragment size and purity was determined by electrophoresis on a 4% Egel agarose gel (Invitrogen). The gel showed a major band corresponding to a fragment of 140 bp (SEQ ID NO:34), matching the expected product which contains SEQ ID NO:12 and terminal restriction sites with tails, provided in the primers, to allow restriction digestion.

Restriction digests for inserting the PCR fragment encoding GeneIII PerS-16KGLG1-6His were the same as for the OmpA PerS construct described in Example 1. Ligation, transformations and sequencing were as previously described. The final clone containing a chimeric gene for expression of the GeneIII PerS-16KGLG1-6His fusion protein from the $P_L$ promoter in *E. coil* was named pLH117.

Example 3

Induction of Expression of the Targeting Signal Sequence-16KGLG1-6His Fusion Proteins Using the PLEX System Shake Flask Studies:

Single colonies of *E. coli* containing pLH117 or pLH119 were grown in Rich Medium overnight at 30° C. at 250 rpm. A fresh culture was started the following day using 10% of the overnight growth diluted in Induction media and grown to an $OD_{550}$ of 0.8. Induction media had no tryptophan (1×M9 salts, 0.2% casamino acids, 0.5% glucose, 1 mM $MgCl_2$, and 100ug/ml ampicillin). To facilitate induction, tryptophan was added for a final concentration of 100 μg/ml and flasks were incubated at 37° C. with shaking at 300 rpm. Samples were taken pre-induction and at 4, 8, and 12 hr post induction. Cell pellets were collected by centrifugation and analyzed for protein production.

Cells expressing the fusion proteins GeneIII targeting signal sequence-16KGLG1-6His (SEQ ID NO:7) or OmpA targeting signal sequence-16KGLG1-6His (SEQ ID NO:6) grew at similar rates as control cells containing only pLEX. Both fusion peptides of the approximate predicted molecular weight of 4 kDa, were readily seen on MemCode Blue (Pierce Chemicals (Rockford, Ill.) stained nitrocellulose blots as seen in FIG. 1; (arrow marks the fusion protein) for samples at 4 and 8 hours post induction, while the control showed no fusion protein at 12 hour post induction. Western blots using an anti-His antibody (Invitrogen, Carlsbad, Calif.), in samples (diluted 1:1) from post induction times confirmed the identity of the indicated band as the fusion protein. Synthetic 16KGLG1+C-terminal 6His tag was used as a standard for quantitation. The control did not express any His tagged proteins. Neither the GeneIII targeting signal sequence nor the OmpA targeting signal sequence appeared to be cleaved from the 16KGLG1 peptide during cellular processing of the protein, indicating that neither targeting signal sequence caused translocation of the 16KGLG1 sequence to the periplasm or external to the cell.

Fermentative Growth:

Ten liter Braun fermenters (B. Braun Biotech, Inc.; Allentown, Pa.) were used to grow and induce a higher biomass of fusion protein producing cells. *E. coli* transformants LH117 and LH119 were grown overnight in 500 ml RM medium in a 2 L flask at 30° C. with shaking at 250 rpm (from 1.5 ml of a −80° C. stock). 500 ml of each overnight inoculum was placed in a 10 L fermenter containing minimal medium (0.3g/L Ferric Ammonium citrate, 2.0 g/L citric acid monohydrate, 7.5g/L potassium biphosphate, 2.0 g/L $MgSO_4$*$7H_2$0, 0.2 g/L $CaCl_2$*2H20, 10ml/L Modified Balch's Trace Elements including the following components (g/L): citric acid*$H_2O$, 4.0; $MnSO_4$*$H_2O$, 3.0; NaCl, 1.0; $FeSO_4$*$7H_2$0, 0.10; $ZnSO_4$*$7H_2$0, 0.10; $CuSO_4$*$5H_2O$, 0.010; $H_3BO_3$, 0.010; and $Na_2MoO_4$*$2H_{2O,}$ 0.010 (Gerhardt, P., et al. [editors]; 1994, Methods for General and Molecular Bacteriology, p. 158, American Society for Microbiology, Washington, D.C.). Initial glucose concentration was 2.0 g/L, ampicillin added to 100 ug/ml. Eight ml/L of Mazu DF204 or comparable antifoam was used.

The following parameters were controlled throughout the fermentation. Dissolved oxygen was maintained at 25%, or at a previously determined set point, through a cascade control scheme that increases agitation first followed by airflow. Pressure was maintained at 0.5 bar (7.5 psig) throughout the run. The pH was controlled at the desired set point, and temperature was maintained at 30° C. until induction at 37° C. $OD_{600}$, pH, and glucose were monitored every 2 hours. Glucose was maintained at approximately 1% by glucose feed. Induction began at mid log phase ($OD_{600}$ of 30), with the addition of 100 μg/ml (1 g/10 L) tryptophan and an increase in temperature from 30° C. to 37° C. $OD_{600}$ at stationary phase of this culture was between 60 and 80 units.

Using these parameters, approximately 100-500 mg of the targeting signal sequence-16KGLG1-6His molecules/L of fermentation culture was produced as shown in the Western blot in FIG. 2. In this assay, synthetic 16KGLG1 with C-terminal 6His tag was used as a standard for quantitation. With the GeneIII targeting signal construct, pLH117, in addition to the expected product there appeared to be a lower band detected with an anti-His antibody. This band may indicate some minor amount of periplasmic processing not detected in the shake flask study.

Example 4

Construction of a Chimeric Gene Encoding a Fusion Protein for Cleavage of the OmpA Periplasmic Targeting Signal from the Antimicrobial Peptide In order to easily separate the OmpA targeting signal sequence peptide from the antimicrobial peptide 16KGLG1, an acid labile site (aspartic acid-proline; DP) was inserted between the two peptide sequences. A DNA fragment encoding the OmpA targeting signal sequence peptide, followed by the acid cleavable recognition site aspartic acid-proline, fused to the 16KGLG1 antimicrobial peptide (SEQ ID NO:13) was synthesized in PCR amplification reactions using the following oligonucleotide primers: SEQ ID NOs:35-38. The primers were reconstituted in $ddH_2O$ to a working concentration of 5 pmoles/μl.

PCR Amplification:

A first round of PCR consisted of 10 pmoles of each of the primers (SEQ ID NOs:35-38), 1×Pfu polymerase buffer (Invitrogen), 0.4 mM dNTPs, and 2 units Pfu polymerase in a 50 μl reaction. A Perkin Elmer thermocycler GENEAMP PCR system 9700 (Perkin Elmer Applies Biosystems; Branchburg, Va.) was used to incubate the reaction as follows: two cycles of: 94° C. melting for 30 sec followed by 46° C. annealing for 30 sec followed by 72° C. extension for 1 min, then 8 cycles of: 94° C. melting for 30 sec followed by 49° C. annealing for 30 sec followed by 72° C. extension for 1 min, with a final extension at 72° C. for 2 min. In a second round of amplification, 5 μl of the first round amplification was used as template. In the second round the use of short, end-sequence specific primers allowed amplification of the entire sequence. The reaction mix contained 20 pmoles of each primer, (SEQ ID#39 and 40), 1×Pfu polymerase buffer, 1 mM dNTPs, and 4 units of Pfu polymerase in a 100 μl volume. The reaction was incubated for 5 cycles of: 94° C. melting for 30 sec followed by 67° C. annealing for 30 sec followed by 72° C. extension for 1 min; then 25 cycles of: 94° C. melting for 30 sec followed by 69° C. annealing for 30 sec followed by 72° C. extension for 1 min; with a final extension at 72° C. for 2 min. Fragment size and purity was determined by electrophoresis on a 4% Egel agarose gel (Invitrogen). The gel showed a major band corresponding to a fragment of 137 bp matching the expected product (SEQ ID NO:41), which contains SEQ ID NO:13 and terminal restriction sites with tails, provided in the primers, to allow restriction digestion.

Cloning of the resulting PCR fragment in the pLEX vector was as described in Example 1. One isolate containing the newly constructed plasmid pLH121 with the correct inserted sequence operably linked for expression from the $P_L$ promoter was used for protein expression studies.

Example 5

Construction of a Chimeric Gene Encoding a Fusion Protein for Cleavage of the GeneIII Periplasmic Targeting Signal from the Antimicrobial Peptide A DNA fragment encoding the GeneIII targeting signal sequence peptide, followed by the acid cleavable recognition site aspartic acid-proline, fused to the 16KGLG1 antimicrobial peptide (SEQ ID NO:14) was synthesized in PCR amplification reactions using the following oligonucleotide primers: SEQ ID NOs:42-47. The primers were reconstituted in $ddH_2O$ to a working concentration of 5 pmoles/μl.

PCR Amplification:

The PCR amplification process was as described previously except primers with SEQ ID NOs:42-45 were used for the first round. The second round of amplification utilized 20 pmoles of each primer, (SEQ ID NOs:46 and 47) to generate a DNA fragment including the sequence of SEQ ID NO:14. Fragment size and purity was determined by electrophoresis on a 4% Egel agarose gel (Invitrogen). The gel showed a major band corresponding to a fragment of 128 bp (SEQ ID NO:48), matching the expected product which contains SEQ ID NO:14 and terminal restriction sites with tails, provided in the primers, to allow restriction digestion. Cloning of the resulting PCR fragment in the PLEX vector was as described in Example 1. The final clone was named pLH122.

Example 6

Expression of the Periplasmic Targeting Signal Sequence-Cleavage site-AMP Fusion Proteins Shake Flask Studies:

Single colonies of *E. coli* containing pLH121 or pLH122 were grown in Rich Medium overnight at 30° C. at 250 rpm. A fresh culture was started the following day using 10% of the overnight growth in Induction medium and grown to an $OD_{550}$ of 1.0 at 37°. To facilitate induction, tryptophan was added for a final concentration of 100 μg/ml. Samples were taken pre-induction and at 5 hr post induction. Cell pellets were collected by centrifugation and analyzed for protein production.

Cells expressing the fusion proteins grew in a similar fashion to control cells containing only the vector, pLEX. The fusion proteins of the approximate predicted molecular weight of 4 kDa, were not present preinduction, but were readily seen on PAGE gels stained with Sypro Orange (Bio-Rad) stain at 2 and 5 hr post induction (FIG. 3; fusion protein indicated by the arrow). Western blots using the 16KGLG1 antibody for detection at 5 hr post induction confirmed the identity of the fusion protein. The signal sequences did not appear to be cleaved from the 16KGLG1 peptide during cellular processing of the protein, as determined by the size of the peptide product, indicating that the peptide did not cross the membrane into the periplasm.

Fermentative Growth of pLH121:

The fermentation of *E. coli* strain pLH121 was carried out as described in Example 3. Using these parameters, in 3 fermentations from 0.6 to 1.2 g per liter of the OmpA targeting signal-Cleavage site-16KGLG1 peptide was produced, as determined by Western blot analysis using the 16KGLG1 antibody (FIG. 4) and synthetic 16KGLG1-6His as a standard. The fusion protein could be seen at 2 hr post induction in both blots stained with MemCode (Pierce) and the Western blots (FIGS. 4A and B, respectively).

A 160 L fermentation of *E. coli* pLH121 was run using the same parameters, which produced approximately 1.2 g/L of the OmpA targeting signal-DP-16KGLG1 fusion protein.

Example 7

Purification of the OmpA Targeting Signal-DP-16KGLG1 Molecule Produced by Fermentation Cell Disruption/Solubilization:

Cells were removed from the fermentation mixture by low speed centrifugation and frozen at −80° for subsequent processing. An average of 40-50 g/L wet cell weight was recovered. Frozen cell paste was resuspended in 10 volumes of phosphate buffered saline, ph 7.2. The slurry was passed three times through a pressure homogenizer (APV Americas, Lake Mills, Wis.) at 12,000 psi with cooling (10-20° C.). Urea was added to the homogenate to give a final concentration of 6 M with stirring and heating to 20° C. The urea homogenate was centrifuged at 12,000×g for 2 hrs at 4° C. Clarified urea supernatant was decanted and stored at 4° C. After overnight storage, the supernatant was centrifuged again at 12,000×g for 2 hrs and the secondary supernatant saved.

Solid Phase Capture of OmpA Targeting Signal-DP-16KGLG1 (SEQ ID NO:4):

Silica based reverse phase packing (DSC18-Supelco) was presoaked in methanol and then mixed with the clarified urea supernatant at a ratio of 1.6 g of resin to 1 gram of wet cell weight. The mixture was stirred and solvent B (95% acetonitrile, 5% water, 0.1% trifuloroacetic acid) was added to give a final concentration of 25% solution B. The mixture was stirred for 30 mins at room temperature. The resin was washed with 5 volumes of 25% solvent B, followed by 5 volumes of 40% solvent B and then 5 volumes of 70% solvent B. Acetonitrile was stripped from the pooled 70% solvent B fractions using rotary evaporation under vacuum at 113 mTorres and 50° C. resulting in an aqueous fraction.

In the 70% B elution fractions three major protein peaks were detected using HPLC analysis as described in the Standard Protocols, corresponding to processed and unprocessed forms of the OmpA targeting signal-DP-16KGLG1 fusion peptide at greater than 92% purity (FIG. 5A). The identities of these peaks were confirmed by MALDI-MS as being peptide with formyl-met (1 peak) and without formyl on the N-terminal met (2 peaks).

Example 8

Acid Cleavage and Isolation of the AMP from the OmpA Targeting Signal Fusion Partner Acid Cleavage:

The aqueous fraction from Example 7 containing 0.1% TFA was heated at 80° C. for 6hrs to cleave at the DP site. The peptides resulting from the cleavage were OmpAPerSD (SEQ ID NO:15) and PG1 (SEQ ID NO:16). Post cleavage, a precipitate of the OmpAD targeting signal peptide was formed.

The solution was chilled to 4° C. for 12 hrs and then spun at 12,000×g for 60 mins to pellet the insoluble OmpA PerS-D fusion partner. Cleavage of the Aspartate/Proline acid labile site was achieved as visualized on HPLC.

Purification Post Cleavage:

P16KGLG1 (PG1; SEQ ID NO:16) in the soluble fraction was further purified using preparative RP-HPLC. A two inch C18 preparative column was used with a gradient of Solvent A (95% water/5% acetonitrile/0.1% TFA) and Solvent B (95% acetonitrile/5% water/0.1% TFA). The column was equilibrated with 90% solvent A and 10% Solvent B. 350 ml of the supernatant from the acid and heat treated product was loaded onto the column using an injector pump at 25 ml/min. The gradient for the preparative run was:

| Time | % A | % B | Flow | Data Aquisition |
|---|---|---|---|---|
| 0:00 | 90 | 10 | 50 ml/min | Start |
| 10:00 | 70 | 30 | 50 ml/min | |
| 50:00 | 30 | 70 | 50 ml/min | End |

The analysis showed one major peak with retention time of 22.0 minutes (42% Solvent B) as shown in FIG. 5B. The peak fractions were collected, quantitated by HPLC (as described in Standard Protocols) and lyophilized for storage. The identity of the peptide was confirmed to be P16KGLG1 (SEQ ID NO:16) by MALDI-MS. The antimicrobial activity of the recombinant P16KGLG1 peptide was identical to chemically synthesized peptide in a static bioassay against *E. coli* 25922 performed as described in the Standard Protocols.

Effect of pH on Solubility of OmpAPerSD and PG1

Stock solutions of chemically synthesized samples of OmpAPerSD and PG1 were made in 0.1N NaOH. Separate samples with pH values between 1 and 12 were prepared as shown in FIG. 6. The pH of each sample was adjusted by the addition of 0.2 M sodium phosphate buffer or 0.1N HCl. Finally, water was added to make the final volume of each sample the same and the samples were mixed by vortexing. After 15 minutes at room temperature all samples were centrifuged at 13,000×g in a micro-centrifuge. The supernatants were carefully separated from the insoluble precipitates and analyzed for protein by the BCA total protein method. Protein determinations were made using standard solutions of synthetic OmpAPerSD and PG1, respectively, in 0.1N NaOH. FIG. 6 shows that the solubility of OmpAPerSD increases with increasing pH. The solubility of PG1 does not appear to be pH dependent within the error of the analysis. The difference in pH solubility of OmpAPerSD and PG1 peptides, with maximal difference at low pH, lends to their ready separation by centrifugation or filtration.

What is claimed is:

1. A composition comprising a fusion protein comprising a periplasmic targeting signal and at least one antimicrobial peptide.

2. A composition of claim 1 wherein the fusion protein has the formula PerS-(C-AMP)$_n$ or PerS-C-(AMP)$_n$ where PerS is a periplasmic targeting signal, C is a cleavage site, AMP is an antimicrobial peptide, and n is an integer from 1 to about 25.

3. A composition of claim 1 wherein the antimicrobial peptide is linear, cationic, amphiphilic, and alpha helical with a molecular weight of less than 6,000 daltons.

4. A composition of claim 3 wherein the antimicrobial peptide is selected from the group consisting of cathelicidins, magainins, cecropins, and non-natural antimicrobial peptides.

5. An isolated nucleic acid fragment encoding the fusion protein of claim 1.

6. A chimeric gene comprising the isolated nucleic acid fragment of claim 5.

7. A vector comprising the chimeric gene of claim 6.

8. A transformed host cell comprising the chimeric gene of claim 7.

9. The transformed host cell of claim 7 wherein the host cell is selected from the group consisting of Gram negative bacteria.

10. The transformed host cell of claim 8 wherein the Gram negative bacteria is selected from the group consisting of *Escherichia, Pseudomonas, Klebsiella, Salmonella, Caulobacter, Methylomonas, Acetobacter, Achromobacter, Acinetobacter, Aeromonas, Agrobacterium, Alcaligenes, Azotobacter, Burkholderia, Citrobacter, Comamonas, Enterobacter, Erwinia, Rhizobium, Vibrio* and *Xanthomonas*.

* * * * *

SEQUENCE LISTING

```
<160> NUMBER OF SEQ ID NOS: 48

<210> SEQ ID NO 1
<211> LENGTH: 16
<212> TYPE: PRT
<213> ORGANISM: artificial
<220> FEATURE:
<223> OTHER INFORMATION: synthetic Antimicrobial peptide

<400> SEQUENCE: 1

Lys Gly Leu Lys Lys Leu Leu Lys Gly Leu Lys Lys Leu Leu Lys Leu
1               5                   10                  15


<210> SEQ ID NO 2
<211> LENGTH: 21
<212> TYPE: PRT
<213> ORGANISM: E. coli

<400> SEQUENCE: 2

Met Lys Lys Thr Ala Ile Ala Ile Ala Val Ala Leu Ala Gly Phe Ala
1               5                   10                  15

Thr Val Ala Gln Ala
            20


<210> SEQ ID NO 3
<211> LENGTH: 18
<212> TYPE: PRT
<213> ORGANISM: bacteriophage fd

<400> SEQUENCE: 3

Met Lys Lys Leu Leu Phe Ala Ile Pro Leu Val Val Pro Phe Tyr Ser
1               5                   10                  15

His Ser
```

-continued

```
<210> SEQ ID NO 4
<211> LENGTH: 39
<212> TYPE: PRT
<213> ORGANISM: artificial
<220> FEATURE:
<223> OTHER INFORMATION: OmpA PerS-DP-G1 fusion protein

<400> SEQUENCE: 4

Met Lys Lys Thr Ala Ile Ala Ile Ala Val Ala Leu Ala Gly Phe Ala
1               5                   10                  15

Thr Val Ala Gln Ala Asp Pro Lys Gly Leu Lys Lys Leu Leu Lys Gly
            20                  25                  30

Leu Lys Lys Leu Leu Lys Leu
        35


<210> SEQ ID NO 5
<211> LENGTH: 36
<212> TYPE: PRT
<213> ORGANISM: artificial
<220> FEATURE:
<223> OTHER INFORMATION: GeneIII PerS-DP-G1 fusion protein

<400> SEQUENCE: 5

Met Lys Lys Leu Leu Phe Ala Ile Pro Leu Val Val Pro Phe Tyr Ser
1               5                   10                  15

His Ser Asp Pro Lys Gly Leu Lys Lys Leu Leu Lys Gly Leu Lys Lys
            20                  25                  30

Leu Leu Lys Leu
        35


<210> SEQ ID NO 6
<211> LENGTH: 43
<212> TYPE: PRT
<213> ORGANISM: artificial
<220> FEATURE:
<223> OTHER INFORMATION: OmpA PerS-G1-6His fusion protein

<400> SEQUENCE: 6

Met Lys Lys Thr Ala Ile Ala Ile Ala Val Ala Leu Ala Gly Phe Ala
1               5                   10                  15

Thr Val Ala Gln Ala Lys Gly Leu Lys Lys Leu Leu Lys Gly Leu Lys
            20                  25                  30

Lys Leu Leu Lys Leu His His His His His His
        35                  40


<210> SEQ ID NO 7
<211> LENGTH: 40
<212> TYPE: PRT
<213> ORGANISM: artificial
<220> FEATURE:
<223> OTHER INFORMATION: GeneIII PerS-G1-6His fusion protein

<400> SEQUENCE: 7

Met Lys Lys Leu Leu Phe Ala Ile Pro Leu Val Val Pro Phe Tyr Ser
1               5                   10                  15

His Ser Lys Gly Leu Lys Lys Leu Leu Lys Gly Leu Lys Lys Leu Leu
            20                  25                  30

Lys Leu His His His His His His
        35                  40


<210> SEQ ID NO 8
<211> LENGTH: 51
<212> TYPE: DNA
```

<213> ORGANISM: artificial
<220> FEATURE:
<223> OTHER INFORMATION: deduced coding sequence for 16KGKG1 peptide

<400> SEQUENCE: 8
aagggactaa agaagttgct gaagggtctg aaaaagctcc tgaagctcta a 51

<210> SEQ ID NO 9
<211> LENGTH: 63
<212> TYPE: DNA
<213> ORGANISM: E. coli

<400> SEQUENCE: 9
atgaaaaaga cagctatcgc aattgcagtg gccttggctg gtttcgctac cgtagcgcaa 60
gct 63

<210> SEQ ID NO 10
<211> LENGTH: 54
<212> TYPE: DNA
<213> ORGANISM: bacteriophage fd

<400> SEQUENCE: 10
atgaaaaaac tgctgttcgc aataccgtta gttgttcctt tctatagcca tagc 54

<210> SEQ ID NO 11
<211> LENGTH: 132
<212> TYPE: DNA
<213> ORGANISM: artificial
<220> FEATURE:
<223> OTHER INFORMATION: Coding for OmpA PerS-G1-6His fusion protein

<400> SEQUENCE: 11
atgaaaaaga cagctatcgc aattgcagtg gccttggctg gtttcgctac cgtagcgcaa 60
gctaagggac taaagaagtt gctgaagggt ctgaaaaagc tcctgaagct ccaccatcat 120
caccatcact aa 132

<210> SEQ ID NO 12
<211> LENGTH: 123
<212> TYPE: DNA
<213> ORGANISM: artificial
<220> FEATURE:
<223> OTHER INFORMATION: Coding for GeneIII PerS-G1-6His fusion protein

<400> SEQUENCE: 12
atgaaaaaac tgctgttcgc aataccgtta gttgttcctt tctatagcca tagcaaggga 60
ctaaagaagt tgctgaaggg tctgaaaaag ctcctgaagc tccaccatca tcaccatcac 120
taa 123

<210> SEQ ID NO 13
<211> LENGTH: 120
<212> TYPE: DNA
<213> ORGANISM: Artificial
<220> FEATURE:
<223> OTHER INFORMATION: Coding for OmpA PerS-DP-G1 fusion protein

<400> SEQUENCE: 13
atgaaaaaga cagctatcgc aattgcagtg gccttggctg gtttcgctac cgtagcgcaa 60
gctgacccga agggactaaa gaagttgctg aagggtctga aaaagctcct gaagctctaa 120

<210> SEQ ID NO 14
<211> LENGTH: 111

-continued

```
<212> TYPE: DNA
<213> ORGANISM: artificial
<220> FEATURE:
<223> OTHER INFORMATION: coding for GeneIII PerS-DP-G1 fusion protein

<400> SEQUENCE: 14

atgaaaaaac tgctgttcgc aataccgtta gttgttcctt tctatagcca tagcgacccg     60

aagggactaa agaagttgct gaagggtctg aaaaagctcc tgaagctcta a            111


<210> SEQ ID NO 15
<211> LENGTH: 22
<212> TYPE: PRT
<213> ORGANISM: artificial
<220> FEATURE:
<223> OTHER INFORMATION: OmpA periplasmic targeting signal peptide
      with aspartate on C-term

<400> SEQUENCE: 15

Met Lys Lys Thr Ala Ile Ala Ile Ala Val Ala Leu Ala Gly Phe Ala
1               5                   10                  15

Thr Val Ala Gln Ala Asp
            20


<210> SEQ ID NO 16
<211> LENGTH: 17
<212> TYPE: PRT
<213> ORGANISM: artificial
<220> FEATURE:
<223> OTHER INFORMATION: 16KGLG1 antimicrobial peptide with proline
      on N-term

<400> SEQUENCE: 16

Pro Lys Gly Leu Lys Lys Leu Leu Lys Gly Leu Lys Lys Leu Leu Lys
1               5                   10                  15

Leu


<210> SEQ ID NO 17
<211> LENGTH: 49
<212> TYPE: DNA
<213> ORGANISM: artificial
<220> FEATURE:
<223> OTHER INFORMATION: synthetic primer

<400> SEQUENCE: 17

gcgccatatg aaaaagacag ctatcgcaat tgcagtggcc ttggctggt                 49


<210> SEQ ID NO 18
<211> LENGTH: 51
<212> TYPE: DNA
<213> ORGANISM: artificial
<220> FEATURE:
<223> OTHER INFORMATION: synthetic priimer

<400> SEQUENCE: 18

ttcgctaccg tagcgcaagc taagggacta aagaagttgc tgaagggtct g              51


<210> SEQ ID NO 19
<211> LENGTH: 49
<212> TYPE: DNA
<213> ORGANISM: artificial
<220> FEATURE:
<223> OTHER INFORMATION: synthetic primer

<400> SEQUENCE: 19

aaaaagctcc tgaagctcca ccatcatcac catcactaag gatcccgcg                 49
```

-continued

<210> SEQ ID NO 20
<211> LENGTH: 42
<212> TYPE: DNA
<213> ORGANISM: artificial
<220> FEATURE:
<223> OTHER INFORMATION: synthetic primer

<400> SEQUENCE: 20
aaggccactg caattgcgat agctgtcttt ttcatatggc gc 42

<210> SEQ ID NO 21
<211> LENGTH: 51
<212> TYPE: DNA
<213> ORGANISM: artificial
<220> FEATURE:
<223> OTHER INFORMATION: synthetic primer

<400> SEQUENCE: 21
ttcagcaact tctttagtcc cttagcttgc gctacggtag cgaaaccagc c 51

<210> SEQ ID NO 22
<211> LENGTH: 56
<212> TYPE: DNA
<213> ORGANISM: artificial
<220> FEATURE:
<223> OTHER INFORMATION: synthetic primer

<400> SEQUENCE: 22
cgcgggatcc ttagtgatgg tgatgatggt ggagcttcag gagctttttc agaccc 56

<210> SEQ ID NO 23
<211> LENGTH: 27
<212> TYPE: DNA
<213> ORGANISM: artificial
<220> FEATURE:
<223> OTHER INFORMATION: synthetic primer

<400> SEQUENCE: 23
gcgccatatg aaaaagacag ctatcgc 27

<210> SEQ ID NO 24
<211> LENGTH: 25
<212> TYPE: DNA
<213> ORGANISM: artificial
<220> FEATURE:
<223> OTHER INFORMATION: synthetic primer

<400> SEQUENCE: 24
cgcgggatcc ttagtgatgg tgatg 25

<210> SEQ ID NO 25
<211> LENGTH: 149
<212> TYPE: DNA
<213> ORGANISM: artificial
<220> FEATURE:
<223> OTHER INFORMATION: PCR frag encoding OmpA PerS-G1-6His

<400> SEQUENCE: 25
gcgccatatg aaaaagacag ctatcgcaat tgcagtggcc ttggctggtt tcgctaccgt 60
agcgcaagct aagggactaa agaagttgct gaagggtctg aaaaagctcc tgaagctcca 120
ccatcatcac catcactaag gatccgcgc 149

<210> SEQ ID NO 26

<211> LENGTH: 24
<212> TYPE: DNA
<213> ORGANISM: artificial
<220> FEATURE:
<223> OTHER INFORMATION: synthetic primer

<400> SEQUENCE: 26
ggtgacgctc ttaaaaatta agcc 24

<210> SEQ ID NO 27
<211> LENGTH: 20
<212> TYPE: DNA
<213> ORGANISM: artificial
<220> FEATURE:
<223> OTHER INFORMATION: synthetic primer

<400> SEQUENCE: 27
ccctgtacga ttactgcagg 20

<210> SEQ ID NO 28
<211> LENGTH: 49
<212> TYPE: DNA
<213> ORGANISM: artificial
<220> FEATURE:
<223> OTHER INFORMATION: synthetic primer

<400> SEQUENCE: 28
gcgccatatg aaaaaactgc tgttcgcaat accgttagtt gttcctttc 49

<210> SEQ ID NO 29
<211> LENGTH: 43
<212> TYPE: DNA
<213> ORGANISM: artificial
<220> FEATURE:
<223> OTHER INFORMATION: synthetic primer

<400> SEQUENCE: 29
gggactaaag aagttgctga agggtctgaa aaagctcctg aag 43

<210> SEQ ID NO 30
<211> LENGTH: 49
<212> TYPE: DNA
<213> ORGANISM: artificial
<220> FEATURE:
<223> OTHER INFORMATION: synthetic primer

<400> SEQUENCE: 30
gcaacttctt tagtcccttg ctatggctat agaaaggaac aactaacgg 49

<210> SEQ ID NO 31
<211> LENGTH: 49
<212> TYPE: DNA
<213> ORGANISM: artificial
<220> FEATURE:
<223> OTHER INFORMATION: synthetic primer

<400> SEQUENCE: 31
cgcgggatcc ttagtgatgg tgatgatggt gcttcaggag ctttttcag 49

<210> SEQ ID NO 32
<211> LENGTH: 27
<212> TYPE: DNA
<213> ORGANISM: artificial
<220> FEATURE:
<223> OTHER INFORMATION: synthetic primer

<400> SEQUENCE: 32

```
gcgccatatg aaaaaactgc tgttcgc                                          27


<210> SEQ ID NO 33
<211> LENGTH: 25
<212> TYPE: DNA
<213> ORGANISM: artificial
<220> FEATURE:
<223> OTHER INFORMATION: synthetic primer

<400> SEQUENCE: 33

cgcgggatcc ttagtgatgg tgatg                                            25


<210> SEQ ID NO 34
<211> LENGTH: 140
<212> TYPE: DNA
<213> ORGANISM: artificial
<220> FEATURE:
<223> OTHER INFORMATION: PCR fragment encoding GeneIII PerS-G1-6His
      fuion protein

<400> SEQUENCE: 34

gcgccatatg aaaaaactgc tgttcgcaat accgttagtt gttcctttct atagccatag     60

caagggacta aagaagttgc tgaagggtct gaaaaagctc ctgaagctcc accatcatca    120

ccatcactaa ggatccgcgc                                                 140


<210> SEQ ID NO 35
<211> LENGTH: 47
<212> TYPE: DNA
<213> ORGANISM: artificial
<220> FEATURE:
<223> OTHER INFORMATION: synthetic primer

<400> SEQUENCE: 35

gcgccatatg aaaaagacag ctatcgcaat tgcagtggcc ttggctg                    47


<210> SEQ ID NO 36
<211> LENGTH: 44
<212> TYPE: DNA
<213> ORGANISM: artificial
<220> FEATURE:
<223> OTHER INFORMATION: synthetic primer

<400> SEQUENCE: 36

cgcaagctga cccgaaggga ctaaagaagt tgctgaaggg tctg                       44


<210> SEQ ID NO 37
<211> LENGTH: 44
<212> TYPE: DNA
<213> ORGANISM: artificial
<220> FEATURE:
<223> OTHER INFORMATION: synthetic primer

<400> SEQUENCE: 37

cgggtcagct tgcgctacgg tagcgaaacc agccaaggcc actg                       44


<210> SEQ ID NO 38
<211> LENGTH: 47
<212> TYPE: DNA
<213> ORGANISM: artificial
<220> FEATURE:
<223> OTHER INFORMATION: synthetic primer

<400> SEQUENCE: 38

cgcgggatcc ttagagcttc aggagctttt tcagaccctt cagcaac                    47
```

<210> SEQ ID NO 39
<211> LENGTH: 26
<212> TYPE: DNA
<213> ORGANISM: artificial
<220> FEATURE:
<223> OTHER INFORMATION: synthetic primer

<400> SEQUENCE: 39
gcgccatatg aaaaagacag ctatcg 26

<210> SEQ ID NO 40
<211> LENGTH: 23
<212> TYPE: DNA
<213> ORGANISM: artificial
<220> FEATURE:
<223> OTHER INFORMATION: synthetic primer

<400> SEQUENCE: 40
cgcgggctcc ttagagcttc agg 23

<210> SEQ ID NO 41
<211> LENGTH: 137
<212> TYPE: DNA
<213> ORGANISM: artificial
<220> FEATURE:
<223> OTHER INFORMATION: PCR fragment encoding OmpA PerS-DP-G1 fusion protein

<400> SEQUENCE: 41
gcgccatatg aaaaagacag ctatcgcaat tgcagtggcc ttggctggtt tcgctaccgt 60
agcgcaagct gacccgaagg gactaaagaa gttgctgaag ggtctgaaaa agctcctgaa 120
gctctaagga tccgcgc 137

<210> SEQ ID NO 42
<211> LENGTH: 49
<212> TYPE: DNA
<213> ORGANISM: artificial
<220> FEATURE:
<223> OTHER INFORMATION: synthetic primer

<400> SEQUENCE: 42
gcgccatatg aaaaaactgc tgttcgcaat accgttagtt gttcctttc 49

<210> SEQ ID NO 43
<211> LENGTH: 47
<212> TYPE: DNA
<213> ORGANISM: artificial
<220> FEATURE:
<223> OTHER INFORMATION: synthetic primer

<400> SEQUENCE: 43
cgacccgaag ggactaaaga agttgctgaa gggtctgaaa aagctcc 47

<210> SEQ ID NO 44
<211> LENGTH: 45
<212> TYPE: DNA
<213> ORGANISM: artificial
<220> FEATURE:
<223> OTHER INFORMATION: synthetic primer

<400> SEQUENCE: 44
tagtcccttc gggtcgctat ggctatagaa aggaacaact aacgg 45

-continued

```
<210> SEQ ID NO 45
<211> LENGTH: 38
<212> TYPE: DNA
<213> ORGANISM: artificial
<220> FEATURE:
<223> OTHER INFORMATION: synthetic primer

<400> SEQUENCE: 45

gcgcggatcc ttagagcttc aggagctttt tcagaccc                             38


<210> SEQ ID NO 46
<211> LENGTH: 25
<212> TYPE: DNA
<213> ORGANISM: artificial
<220> FEATURE:
<223> OTHER INFORMATION: synthetic primer

<400> SEQUENCE: 46

gcgccatatg aaaaaactgc tgttc                                           25


<210> SEQ ID NO 47
<211> LENGTH: 22
<212> TYPE: DNA
<213> ORGANISM: artificial
<220> FEATURE:
<223> OTHER INFORMATION: synthetic primer

<400> SEQUENCE: 47

gcgcggatcc ttagagcttc ag                                              22


<210> SEQ ID NO 48
<211> LENGTH: 128
<212> TYPE: DNA
<213> ORGANISM: artificial
<220> FEATURE:
<223> OTHER INFORMATION: PCR fragment encoding GeneIII PerS-DP-G1
      fusion protein

<400> SEQUENCE: 48

gcgccatatg aaaaaactgc tgttcgcaat accgttagtt gttcctttct atagccatag     60

cgacccgaag ggactaaaga agttgctgaa gggtctgaaa aagctcctga agctctaagg    120

atccgcgc                                                             128
```